US006922481B2

(12) United States Patent
Masuda et al.

(10) Patent No.: US 6,922,481 B2
(45) Date of Patent: Jul. 26, 2005

(54) PROGRAMMING APPARATUS OF A VISUAL INSPECTION PROGRAM

(75) Inventors: Tsuyoshi Masuda, Osaka (JP); Mitsuru Shirasawa, Shijonawate (JP)

(73) Assignee: Matsushita Electric Works, Ltd., Osaka (JP)

( * ) Notice: Subject to any disclaimer, the term of this patent is extended or adjusted under 35 U.S.C. 154(b) by 650 days.

(21) Appl. No.: 10/048,492

(22) PCT Filed: May 25, 2001

(86) PCT No.: PCT/JP01/04420

§ 371 (c)(1),
(2), (4) Date: Mar. 27, 2002

(87) PCT Pub. No.: WO02/01208

PCT Pub. Date: Jan. 3, 2002

(65) Prior Publication Data

US 2002/0122582 A1 Sep. 5, 2002

(30) Foreign Application Priority Data

Jun. 27, 2000 (JP) ..................... 2000-193408

(51) Int. Cl.[7] ............................................. G06K 9/00
(52) U.S. Cl. .................. 382/141; 382/149; 348/86; 348/125; 702/35
(58) Field of Search ............................. 382/141, 152, 382/145, 149; 348/86, 87, 92, 125, 126; 702/35, 118, 123; 700/95, 109, 110, 175; 356/237.1

(56) References Cited

U.S. PATENT DOCUMENTS

| 5,424,838 A | 6/1995 | Siu |
| 5,615,219 A | 3/1997 | Keating et al. |
| 5,963,662 A | 10/1999 | Vachtsevanos et al. |
| 6,055,369 A * | 4/2000 | Sawahata et al. ............ 717/109 |
| 6,298,474 B1 * | 10/2001 | Blowers et al. .............. 717/104 |
| 6,597,381 B1 * | 7/2003 | Eskridge et al. ............. 715/804 |

FOREIGN PATENT DOCUMENTS

| JP | 63191278 | 8/1988 |
| WO | 99/16010 | 4/1999 |

OTHER PUBLICATIONS

An article by Di Mauro et al. "Check! A Generic and Specific Industrial Inspection Tool", IEEE Proceedings: Vision, Image and Signal Processing, Institution of Electrical Engineers, GB, vol. 143, No. 4, Aug. 1, 1996, pp. 241–249.
English language Abstract for JP 63–191278.

* cited by examiner

*Primary Examiner*—Bhavesh M. Mehta
*Assistant Examiner*—John Strege
(74) *Attorney, Agent, or Firm*—Greenblum & Bernstein, P.L.C.

(57) ABSTRACT

A programming apparatus supports a user to program a visual inspection program used in a visual inspection apparatus. A plurality of standard inspection flows corresponding to kinds of products to be inspected, a plurality of image processing algorithms and a plurality of inspection parameters used in the visual inspection of the product are previously memorized. The user prepares a plurality of image data of defective units and non-defective units of the product which he wishes to inspect, and programs a provisional visual inspection program configured by the standard inspection flow corresponding to the kind of the product which is selected by the user, the image processing algorithms and the inspection parameters selected by following a guidance of the standard inspection flow. The provisional visual inspection program is evaluated by using the sample image data whether it is proper or improper for inspecting the product.

26 Claims, 26 Drawing Sheets

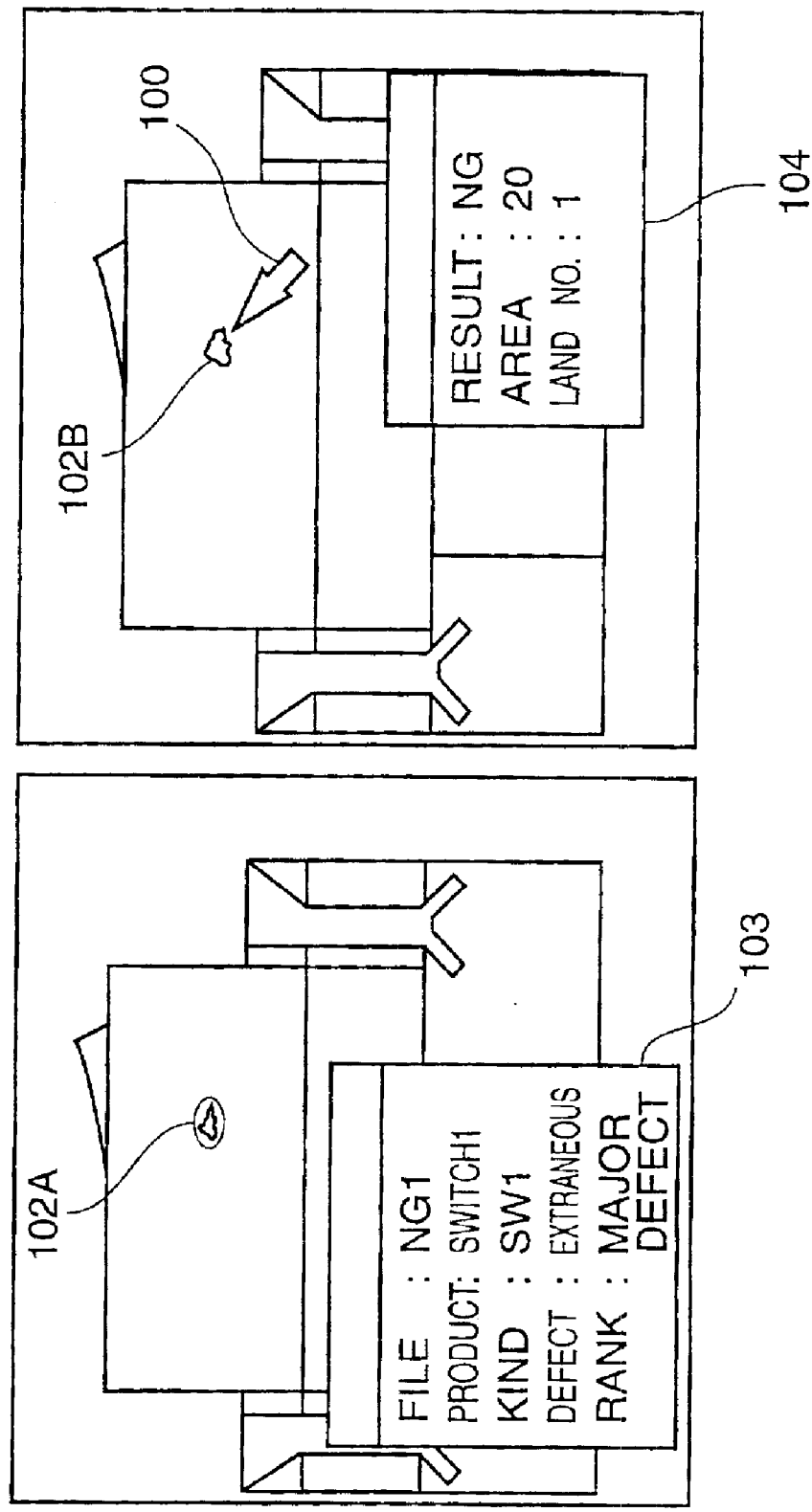

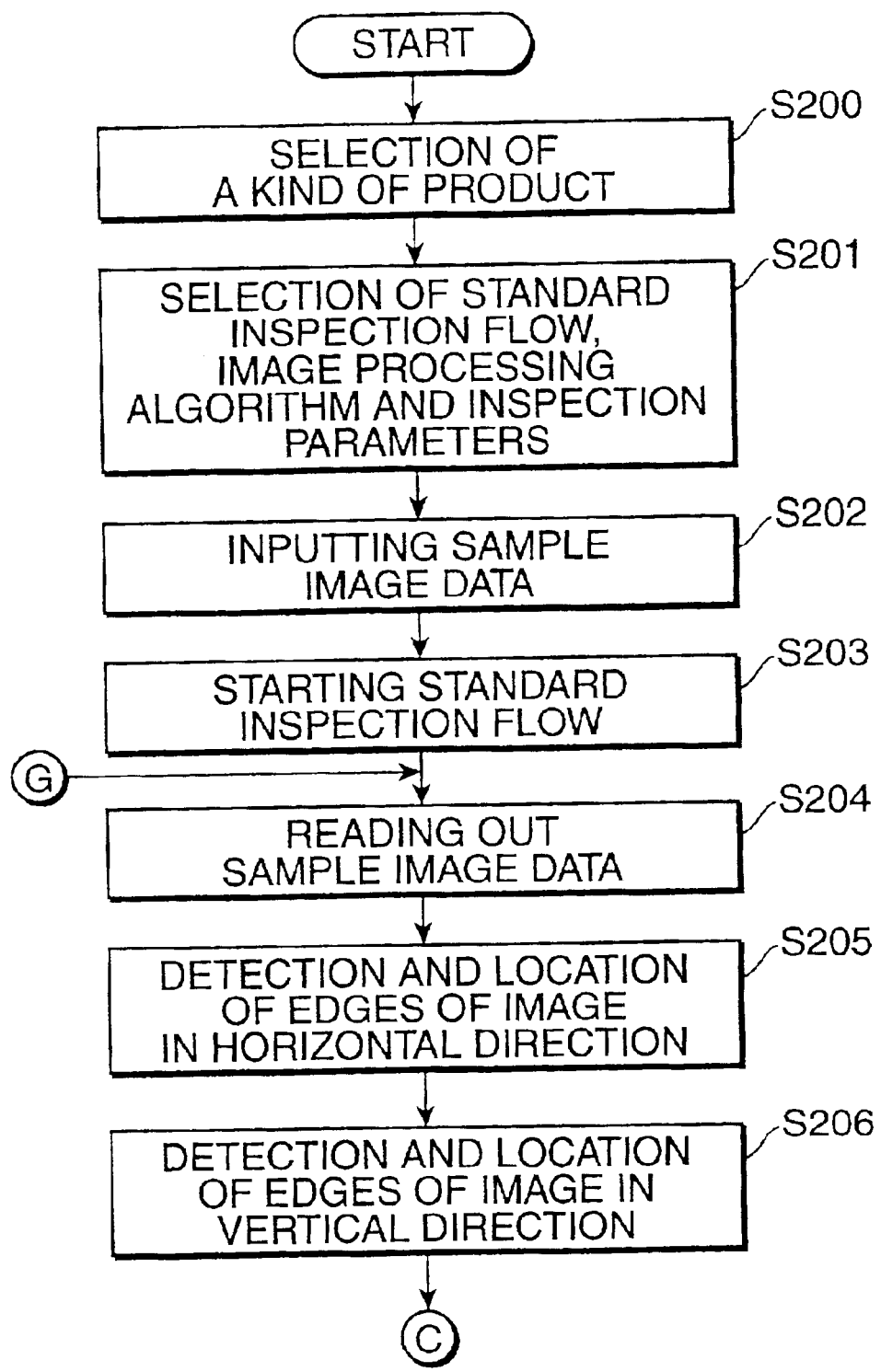

FIG. 15

| PARAMETERS | PRECE-DENCES | INITIAL VALUES | WIDTH | DIRECTION | LIMITATION | |
|---|---|---|---|---|---|---|
| | | | | | LOWER | UPPER |
| THRESHOLD VALUE OF EDGE DETECTION | 1 | 50 | 5 | ± | 2 | 100 |
| THRESHOLD VALUE OF EDGE EXTENSION | 3 | 30 | 5 | ± | 10 | 50 |
| THRESHOLD VALUE OF DIFFERENTIAL | 2 | 4 | 1 | ± | 1 | 10 |
| THRESHOLD VALUE OF SUM OF DIFFERENTIAL | 2 | 50 | 10 | + | 50 | 200 |
| DIFFERENTIAL DIRECTION (1 TO 8) | 3 | 1 | 1 | + | 1 | 8 |

FIG. 17

RESULTS OF INSPECTION OF SWITCH

| NON-DEFECTIVE | | NON-DEFECTIVE IMAGE | | | | | | | GOOD | NO GOOD |
|---|---|---|---|---|---|---|---|---|---|---|
| ALGORITHMS | | 1 | 2 | 3 | 4 | 5 | 6 | 7 | | |
| CRACK | | ○ | ○ | ○ | ○ | ○ | ○ | ○ | 7/7 | 0/7 |
| CHIPPING | | ○ | ○ | × | ○ | ○ | ○ | ○ | 6/7 | 1/7 |
| EXTRANEOUS MATTER | | ○ | ○ | ○ | ○ | ○ | ○ | ○ | 7/7 | 0/7 |
| SCRATCH | | ○ | ○ | ○ | ○ | ○ | × | ○ | 6/7 | 1/7 |

B1  B2  B3

| DEFECTIVE | CRACK DEFECT | | | EXTRANEOUS DEFECT | | | GOOD | NO GOOD |
|---|---|---|---|---|---|---|---|---|
| ALGORITHMS | 1 | 2 | 3 | 4 | 1 | 2 | 3 | | |
| CRACK | ○ | ○ | × | ○ | ○ | × | ○ | 5/7 | 2/7 |
| CHIPPING | × | ○ | × | × | ○ | ○ | ○ | 5/7 | 2/7 |
| EXTRANEOUS MATTER | ○ | ○ | ○ | ○ | ○ | ○ | ○ | 6/7 | 1/7 |
| SCRATCH | ○ | ○ | ○ | ○ | ○ | ○ | ○ | 6/7 | 0/7 |

B4  B5  100

PROGRAMMING APPARATUS OF A VISUAL INSPECTION PROGRAM

TECHNICAL FIELD

The present invention relates to an apparatus for programming a visual inspection program used in a visual inspection apparatus for inspecting an appearance of a product conveyed on a manufacturing line thereof.

BACKGROUND ART

Conventionally, a visual inspection apparatus is used for inspecting an appearance of a product in a manufacturing processes. In the conventional visual inspection apparatus, a visual image of an appearance of a product is taken by a camera using an image acquisition device such as a CCD (Charge Coupled device), and an image data corresponding to the visual image of the product outputted from the camera is processed by following a predetermined visual inspection program so that it is judged whether the appearance of the product satisfies a predetermined quality or not.

Prior to the actual visual inspection of the products, the visual inspection program and the parameters are adjusted in a manner so that the appearance of the products are precisely judged as defective or non-defective by using sample image data of defective units and non-defective units which are previously prepared by a user of the visual inspection apparatus.

There are infinite varieties in the products to be inspected, so that inspection items, inspection methods, and inspection parameters cannot be standardized. Thus, the visual inspection program generally has an exclusive use with respect to each product to be inspected. When the kind of the product to be inspected is changed, it is necessary to prepare a new exclusive visual inspection program suitable for inspecting the new product. Furthermore, it demands an expert knowledge with respect to a computer such as the C-language to program the visual inspection program, so that the visual inspection program is generally programmed by a programmer in a vendor of the visual inspection apparatus.

On the other hand, the Publication Gazette of Unexamined Japanese Patent Application Sho 63-191278 shows a conventional user support method in an interactive image processing system by which the user unaccustomed to the image processing algorithm can easily execute the image processing. In the interactive image processing system, the know-how of an expert in the art of the image processing with respect to the usage or the operational specification of the image processing algorithms is memorized in a memory. When the user is required to select a sub-function of the image processing or to set a parameter while the image processing algorithm is executed, the user is supported by displaying the explanation of judging standard for selecting the sub-function or the parameter on a monitor display, or supported by automatically selecting the sub-function or the parameter by using the know-how of the expert in the memory.

The conventional user support method can support the user exactly for selecting the most suitable sub-function or parameter in the image processing. It, however, is difficult to support the user of the visual inspection apparatus for programming the visual inspection program easily, even when the conventional user support method is applied to the method for forming the visual inspection program. Since the visual inspection program has substantially the exclusive use with respect to the product to be inspected, the know-how of the expert can only be applied to a specific case. Thus, it is substantially impossible that the user unaccustomed to the expert knowledge of the computer can easily program the visual inspection program suitable for the visual inspection of the desired product.

Furthermore, when the product to be inspected is changed, the image data to be processed in the visual inspection program will be different at all. If the inspection parameters used in the visual inspection program are not based on the actual image data of the product to be inspected, the reliability and the precision of the visual inspection will be reduced. Still furthermore, if the inspection result by the image processing steps in the visual inspection are not previously confirmed, the results of the visual inspection becomes unreliable.

DISCLOSURE OF INVENTION

An objective of the present invention is to provide a programming apparatus of a visual inspection program used in a visual inspection apparatus, by which the user of the visual inspection apparatus can easily program the visual inspection program suitable for an object (or a product) to be inspected. Another objective of the present invention is to provide a visual inspection apparatus by which the reliable and precise visual inspection suitable for inspecting the object can be executed. Still another objective of the present invention is to provide a method for programming a visual inspection program by which the user of the visual inspection apparatus can easily program the visual inspection program suitable for the object to be inspected. Still another objective of the present invention is to provide a program for programming the visual inspection program, which can be installed into a known personal computer so that the known personal computer can serve as the programming apparatus of the visual inspection program. Still another objective of the present invention is to provide a recording medium memorizing the program for programming the visual inspection program.

A programming apparatus of a visual inspection program in accordance with the present invention comprises: an image data memory for memorizing a plurality of sample image data of defective units and non-defective units of an object to be inspected which are previously prepared by a user; an algorithm memory for memorizing a plurality of image processing algorithms with respect to each inspection item; a standard flow memory for memorizing at least one standard inspection flow and a plurality of inspection parameters with respect to each kind of object to be inspected; a display unit having a monitor display for displaying at least a guidance of a programming steps; an input unit by which a user inputs or selects a kind of an object which he wishes to inspect, selects at least one image processing algorithm and at least one inspection parameter used in a standard inspection flow automatically selected corresponding to the kind of the object; and an inspection processor for controlling whole of the programming apparatus and for executing the following processes.

The inspection processor displays the guidance of the programming steps, and automatically selects a standard inspection flow from the standard flow memory corresponding to the input or selection of the kind of the object by the user. Subsequently, the inspection processor reads out at least one image processing algorithm from the algorithm memory and at least one inspection parameter from the standard flow memory corresponding to the selection by the user, so that the inspection processor programs a provisional visual inspection program by using the standard inspection flow, the image processing algorithm(s) and the inspection parameter(s). When the provisional visual inspection program is programmed, the inspection processor processes the sample image data of defective units and non-defective units by following the provisional visual inspection program, and executes the visual inspection whether an appearance of the object with respect to each sample image data is defective or non-defective using processed image data. The inspection processor displays the results of the visual inspection of the sample image data on the monitor display of the display unit. Furthermore, the inspection processor requires the user whether the provisional visual inspection program is proper or improper. When the user is satisfied by the result of the visual inspection of the sample image data, the inspection processor outputs the provisional visual inspection program is outputted as a final visual inspection program used in the visual inspection apparatus. Alternatively, when the user is not satisfied by the result of the visual inspection of the sample image data, the inspection processor further requires the user to change at least one image processing algorithm and/or at least one inspection parameter until the provisional visual inspection program will be judged proper.

By such a configuration, the user of the visual inspection apparatus unaccustomed to the programming language and/or the image processing can easily program the visual inspection program suitable for inspecting the optional object he wishes to inspect. Especially, the sample image data of the defective units and non-defective units of the object are actually inspected by using the provisional visual inspection program, so that it can easily be judged whether the provisional visual inspection program is proper or improper by considering the result of the inspection. Furthermore, when the provisional visual inspection program is judged improper, it is possible to compensate the provisional visual inspection program until it is judged proper by changing the image processing algorism and/or the inspection parameters.

A visual inspection apparatus in accordance with the present invention comprises: an image acquisition unit for taking a visual image of an object conveyed on a manufacturing line thereof; and a removing unit for removing or for instructing to remove an object judged defective from the manufacturing line, further to the above-mentioned function of the programming apparatus of the visual inspection program.

By such a configuration, the user of the visual inspection apparatus can directly program the visual inspection program into a memory of the visual inspection apparatus. Thus, when the object to be inspected is changed, the user can easily change the visual inspection program suitable for inspecting the optional object he wishes to inspect.

A method for programming a visual inspection program in accordance with the present invention comprises the steps of: memorizing a plurality of image processing algorithm with respect to each inspection item, at least one standard inspection flow and a plurality of inspection parameters with respect to each kind of object to be inspected; requiring the user to input or to select a kind of the object to be inspected; requiring the user to input a plurality of sample image data of defective units and non-defective units of objects to be inspected; automatically selecting a standard inspection flow corresponding to the kind of the object among the previously memorized standard inspection flows; requiring the user to select at least one image processing algorithm and at least one inspection parameter among the previously memorized image processing algorithms and the inspection parameters by following the selected standard inspection flow; programming a provisional visual inspection program using the elected standard inspection flow, the image processing algorithm(s) and the inspection parameter(s); reading out the sample image data one by one; executing visual inspection of the sample image data by following the provisional visual inspection program; executing the visual inspection with respect to each sample image data whether an appearance of the object is defective or non-defective; and displaying the result of the judgment of the visual inspection of the sample image data on the monitor display.

By such a configuration, the user unaccustomed to the programming language and/or the image processing can easily program the visual inspection program suitable for inspecting the optional object he wishes to inspect by following the requirement in the programming method. Furthermore, the visual inspection program programmed by this method is evaluated by actually executing the visual inspection with respect to the sample image data, so that the visual inspection program used in the visual inspection apparatus becomes reliable and precise.

A program for programming the visual inspection program in accordance with the present invention comprises the steps of: requiring a user to input or to select a kind of an object to be inspected; automatically selecting a standard inspection flow among a plurality of standard inspection flows previously inputted corresponding to the input or selection of the kind of the object by the user; requiring the user to input at plurality of sample image data of the object including at least one defective unit and at least one non-defective unit; requiring the user to select at least one image processing algorithm and at least one inspection parameter among a plurality of image processing algorithms and a plurality of inspection parameters previously inputted; programming a provisional visual inspection program using the selected standard inspection flow, the image processing algorithm(s) and the inspection parameter(s); reading the sample image data one by one; executing the visual inspection with each sample image data by following the provisional visual inspection program; judging whether the sample image data is defective or non-defective; and displaying the result of the judgment with respect to all the sample image data on a monitor display.

By such a configuration, when the program is installed into a known personal computer, the personal computer can be used as the programming apparatus of the visual inspection apparatus in accordance with the present invention. The program can be downloaded from a server of the vender supplying the visual inspection apparatus, so that the user can easily program the visual inspection program suitable for the optional object which the user wishes to inspect, at any time.

A recording medium in accordance with the present invention memorizes at least one standard inspection flow with respect to each kind of object to be inspected, a plurality of image processing algorithm with respect to each inspection item, a plurality inspection parameters and a program for programming a visual inspection program. The program comprises the steps of: requiring a user to input or to select a kind of the object to be inspected; requiring the user to input a plurality of sample image data of defective units and non-defective units of objects to be inspected which are previously prepared by a user; automatically selecting a standard inspection flow corresponding to the kind of the object among the previously memorized standard inspection flows; requiring the user to select at least one image processing algorithms and at least one inspection parameter among the previously memorized image processing algorithms and the inspection parameters by following the selected standard inspection flow; programming a provisional visual inspection program using the selected standard inspection flow, the image processing algorithm(s) and the inspection parameter(s); reading out the sample image data one by one for executing visual inspection by following a provisional visual inspection program configured by the elected standard inspection flow, the image processing algorithm(s) and the inspection parameter(s); executing the visual inspection with respect to each sample image data whether an appearance of the object is defective or non-defective by following the provisional visual inspection program; and displaying the result of the judgment of the visual inspection of the sample image data on the monitor display.

By such a configuration, the user already has the visual inspection apparatus can easily program the visual inspection program suitable for the optional object which the user wishes to inspect, after the purchase of the visual inspection apparatus.

BRIEF DESCRIPTION OF DRAWINGS

FIG. 12 is a drawing for showing images of the product before and after image processing in the programming steps of the visual inspection program in the first embodiment;

FIGS. 13A to 13C are drawings for showing a flowchart of a first modification of the programming steps of the visual inspection program in the first embodiment;

FIG. 15 is a drawing for showing a table of inspection parameters and specific values thereof in the second modification of the programming steps of the visual inspection program in the first embodiment;

FIG. 17 is a drawing for showing a table of judgments of sample image data used in the programming steps of the visual inspection program with respect to respective image processing algorithms in the first embodiment;

BEST MODE FOR CARRYING OUT THE INVENTION

A first embodiment of the present invention is described. A programming apparatus of a visual inspection program in accordance with the present invention supports a user of a visual inspection apparatus easily for programming the visual inspection program used in the visual inspection apparatus and suitable for inspecting products conveyed on a manufacturing line.

In this embodiments, it is possible that the programming apparatus is independent from the visual inspection apparatus. Alternatively, it is possible that the programming apparatus is included in the visual inspection apparatus. In the former case, a program for programming the visual inspection program can be installed in a known apparatus such as a personal computer or a dedicated apparatus described below. In the latter case, a processing unit of the visual inspection apparatus serves as the programming apparatus.

Figure 1:
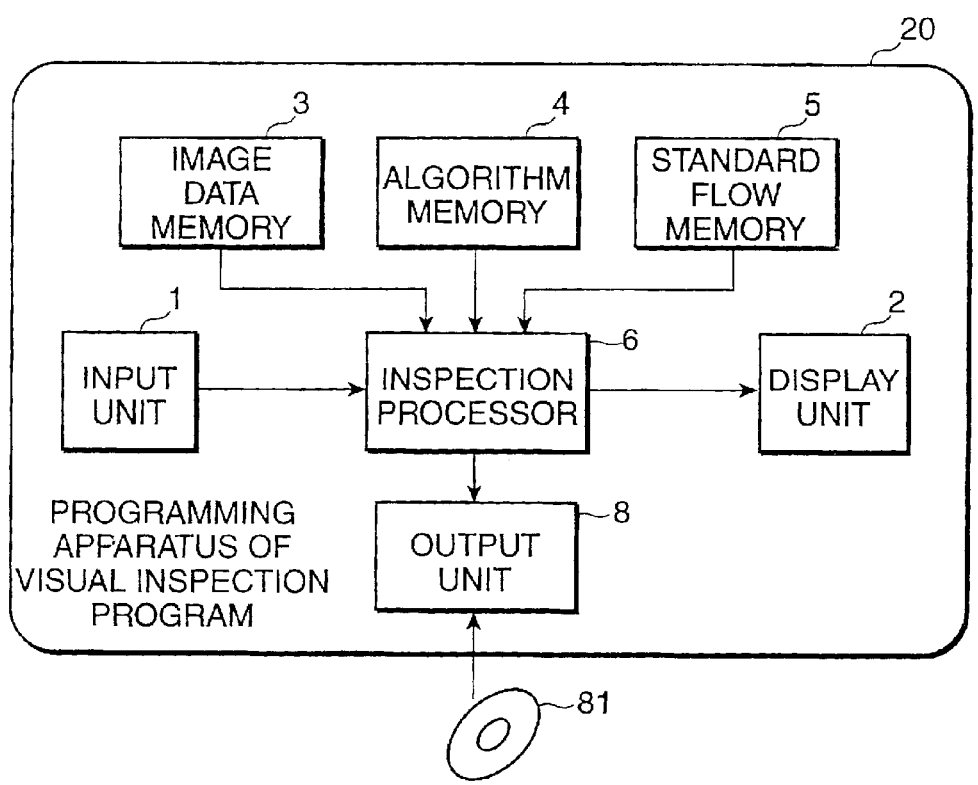
FIG. 1 is a block diagram for showing a configuration of a programming apparatus of a visual inspection program in accordance with a first embodiment of the present invention.
Figure 2:
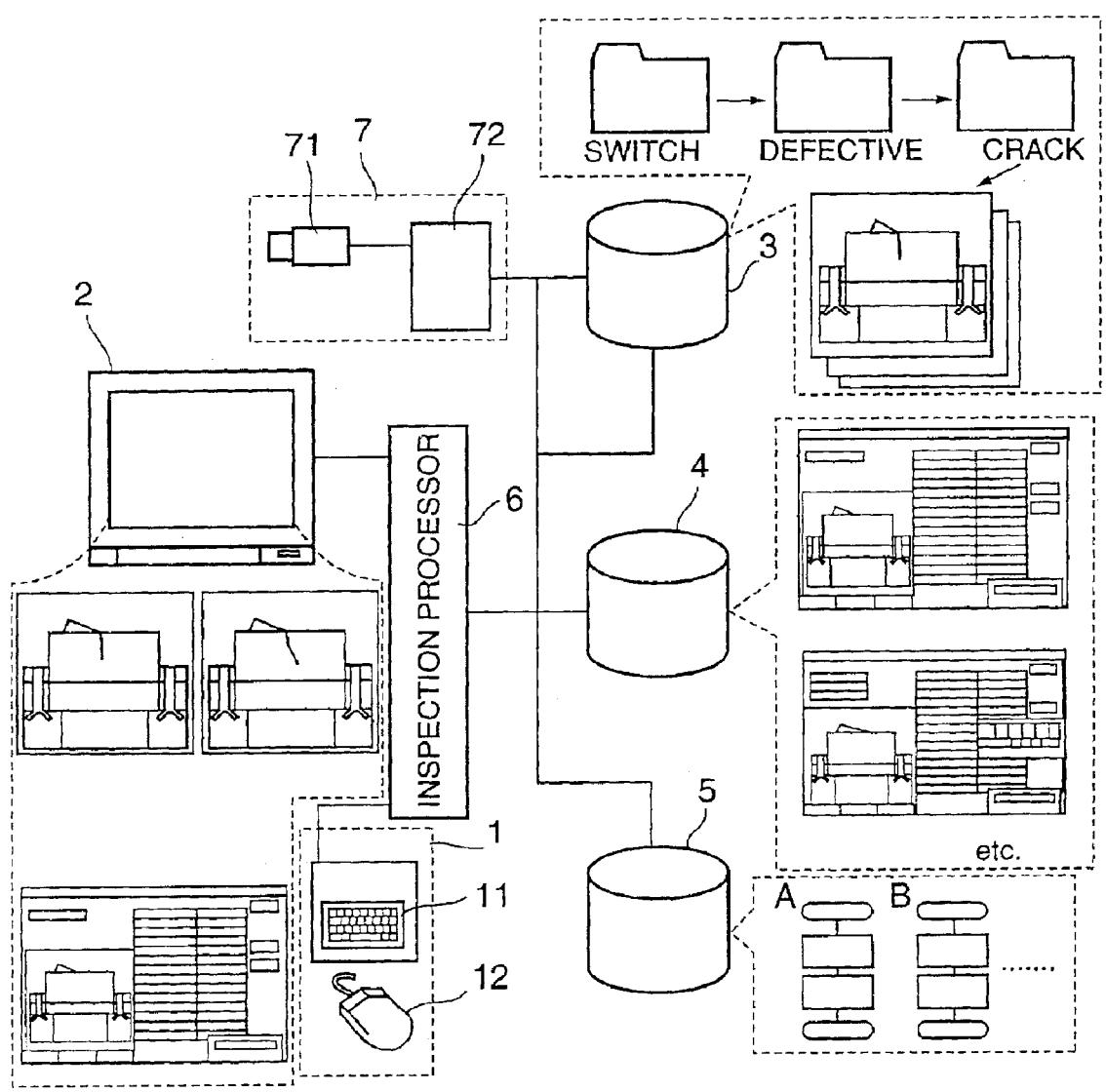
FIG. 2 is a drawing schematically for showing contents of each block of the programming apparatus in the first embodiment.

FIG. 1 shows a block diagram of the programming apparatus 20 in the first embodiment. FIG. 2 visually shows the contents of each block of the programming apparatus 20.

An input unit 1 is configured by a key board 11, a mouse 12 and so on, by which the user of the programming apparatus 20 can input, for example, his judgment with respect to a result of a visual inspection, or his selection of parameters and image processing algorithms, and so on used in the visual inspection steps. A display unit 2 is configured by a monitor display such as a CRT (Cathode Ray Tube apparatus) or a LCD (Liquid Crystal Display apparatus) for displaying visual images of the products to be inspected before and after the image processing, or for displaying a guidance of input operation for programming the visual inspection program.

An image data memory 3 is configured by a recording and reproducing apparatus for recording and reading the image data on and from a recording medium such as a hard disc, a magneto-optical disk (MO disc) or a magnetic disc. The image data memory 3 memorizes the image data of defective units and non-defective units which are previously taken by the user with using an image acquisition unit 7. The image acquisition unit 7 is configured by a camera 71 using an image acquisition device such as CCD and a signal processor 72. Samples of the defective units and the non-defective units of the products to be inspected are prepared by the user.

In the image data memory 3, hierarchical folders are provided. When the product to be inspected is a switch, a folder named "DEFECTIVE" for memorizing the image data of the defective units and a folder named "NON-DEFECTIVE" for memorizing the image data of the non-defective units are provided below a folder named "SWITCH", as shown in FIG. 2. Furthermore, a plurality of folders named "CRACK" and so on corresponding to the causes of the defective such as an occurrence of a crack, an extraneous matter, and so on are provided below the folder named "DEFECTIVE".

An algorithm memory 4 is configured by a recording and reproducing apparatus for recording and reading the image data on and from a recording medium such as a hard disc, an MO disk or a magnetic disc. The algorithm memory 4 memorizes a plurality of image processing algorithms (inspection items) used for inspection of tinted extraneous matter, occurrence of crack, and so on with respect to each product to be inspected. The image processing algorithms are selected by the user in the programming process of the visual inspection program suitable for the inspection of the products.

A standard flow memory 5 is configured by a recording and reproducing apparatus for recording and reading the image data on and from a recording medium such as a hard disc, a magneto-optical disk or a magnetic disc. The standard flow memory 5 memorizes a plurality of standard inspection flows and inspection parameters respectively suitable for kinds of products to be inspected such as a switch, a circuit breaker or a receptacle. The standard inspection flows are previously prepared by, for example, a programmer in the vendor of the visual inspection apparatus responding to the request of the user who wishes to inspect his products, visually. Details of the standard inspection program will be described below.

The image data memory 3, the algorithm memory 4 and the standard flow memory 5 can be configured by the same recording and reproducing apparatus. Alternatively, they can respectively be configured by independent recording and reproducing apparatuses.

An inspection processor 6 is configured by a CPU (Central Processing Unit), a memory and a control program for controlling the programming apparatus of the visual inspection program. The inspection processor 6 is used not only for controlling the elements of the programming apparatus 20 wholly, but also for executing the programming steps of the visual inspection program by the programming apparatus 20.

An output unit 8 is configured by a recording apparatus for recording the visual inspection program programmed by the programming apparatus 20 into a recording medium 81 such as a CD-R (Compact Disc Recordable), an MO disc, a floppy disc, or the like.

Figure 3:
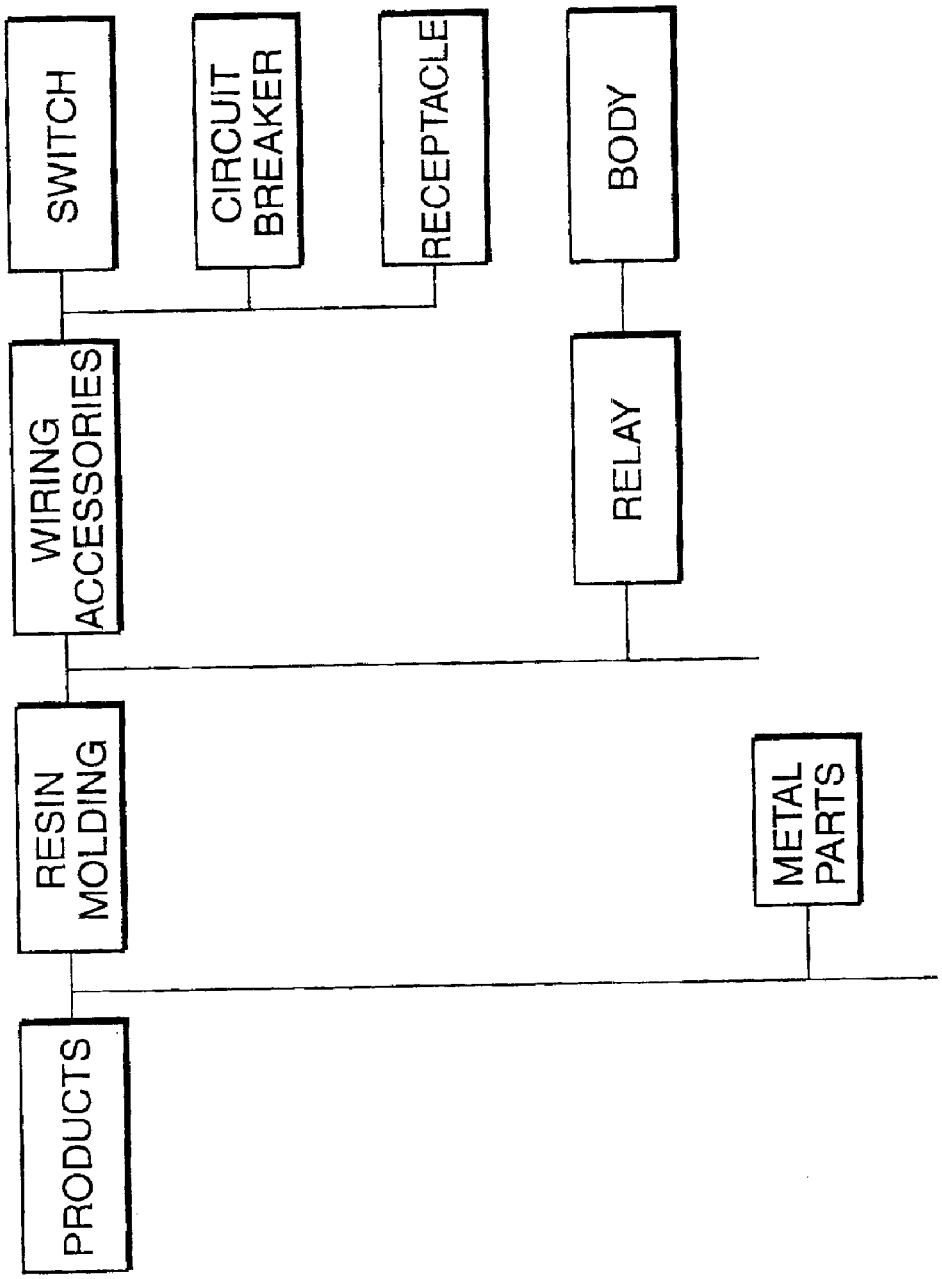
FIG. 3 is a block diagram for showing examples of kinds of products to be inspected in the first embodiment.

FIG. 3 shows examples of the kinds of the products to be inspected. The standard flow memory 5 memorizes the standard inspection flows and the inspection parameters used in respective standard inspection flows corresponding to the lowest hierarchical names of the products. The kinds of the products are sorted corresponding to the materials of the surface of the products at first stage. Furthermore, the kinds of the products are sorted corresponding to the use of the products at second stage. Still furthermore, the kinds of the products are sorted by the trade name or the parts name of the products at third stage.

Figure 4:
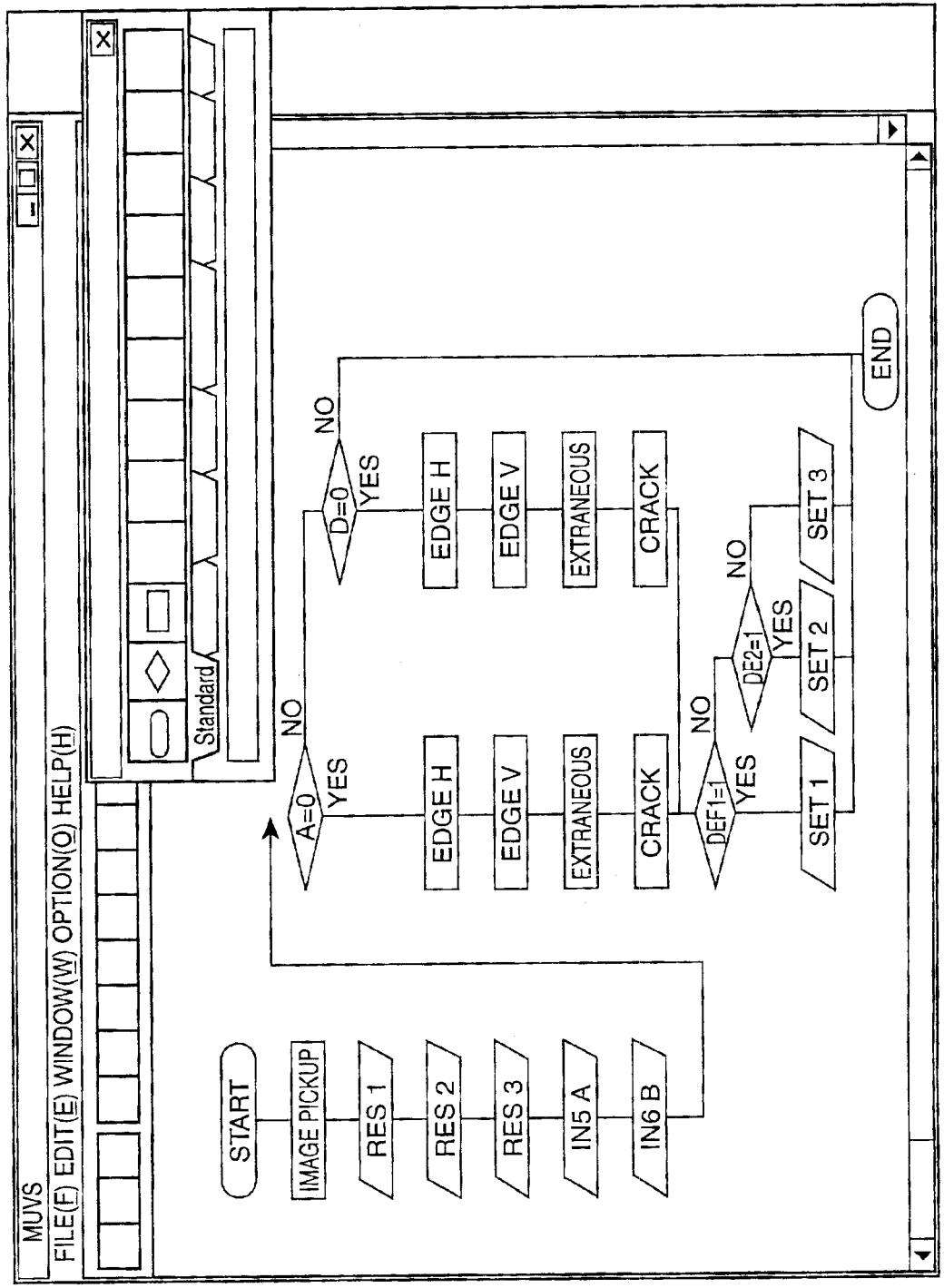
FIG. 4 is a drawing for showing an example of a display of a standard inspection flow on a display unit of the programming apparatus in the first embodiment.

FIG. 4 shows an example of a guidance of programming steps displayed on the monitor display of the display unit 2, when the standard inspection flow suitable for visual inspection of the switch is read out from the standard flow memory 5. Since the guidance is displayed on the display unit 2, so that the user can serially input the image data and select the inspection items and/or the inspection parameters by following the instruction in the guidance.

Figure 5:
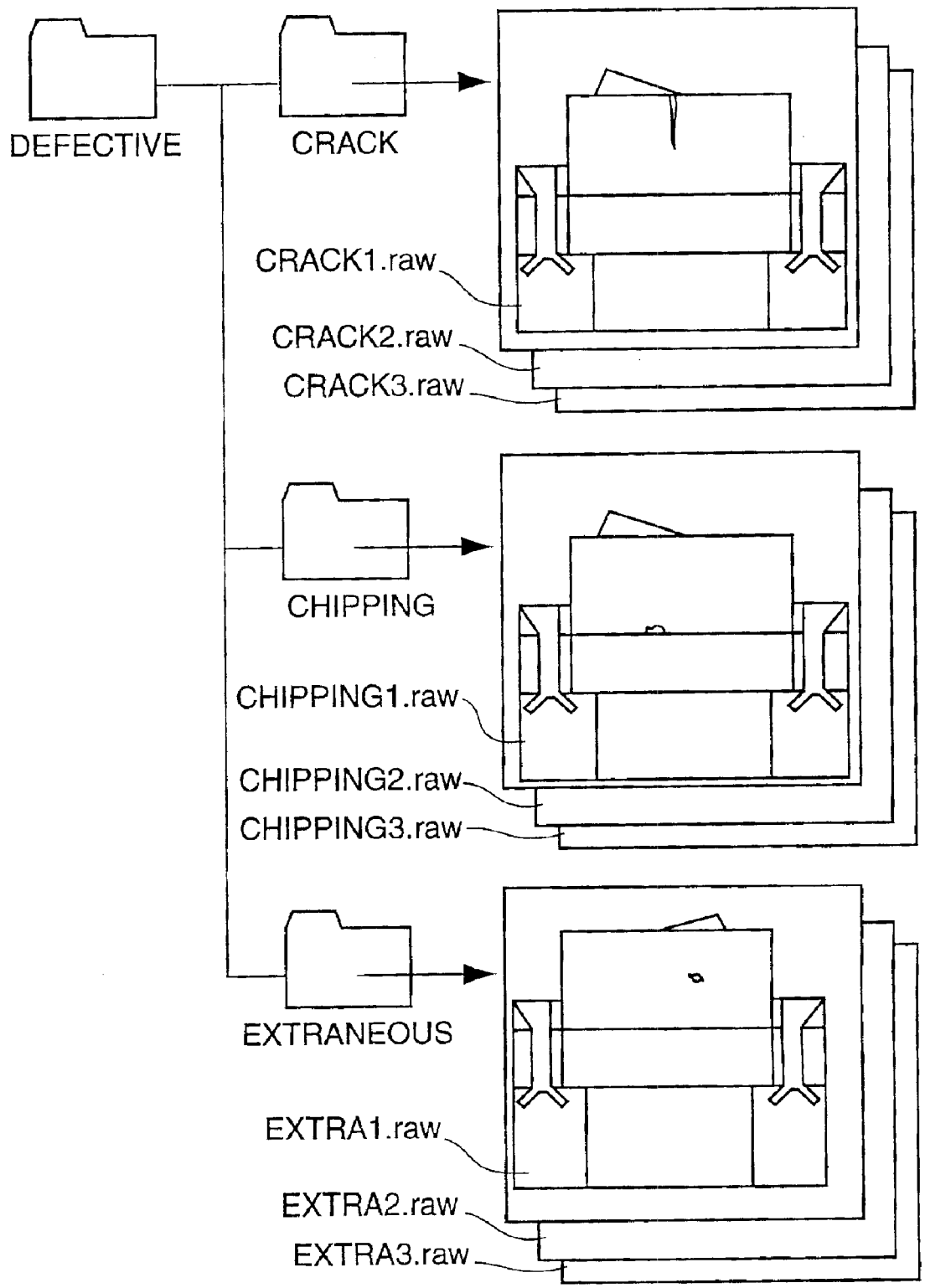
FIG. 5 is a block diagram for showing folders and examples of image data of defective units memorized in the folders in the first embodiment.

FIG. 5 shows examples of the image data of the defective units of the switches. Three folders named "CRACK", "CHIPPING" and "EXTRANEOUS" are provided below the folder "DEFECTIVE". Image data of the samples of the defective units of the switches are taken by the user by using the image acquisition unit 7 prior to the programming of the visual inspection program. The image data are sorted corresponding to the kinds of the defect and memorized in the folder corresponding to the defect.

Figure 6:
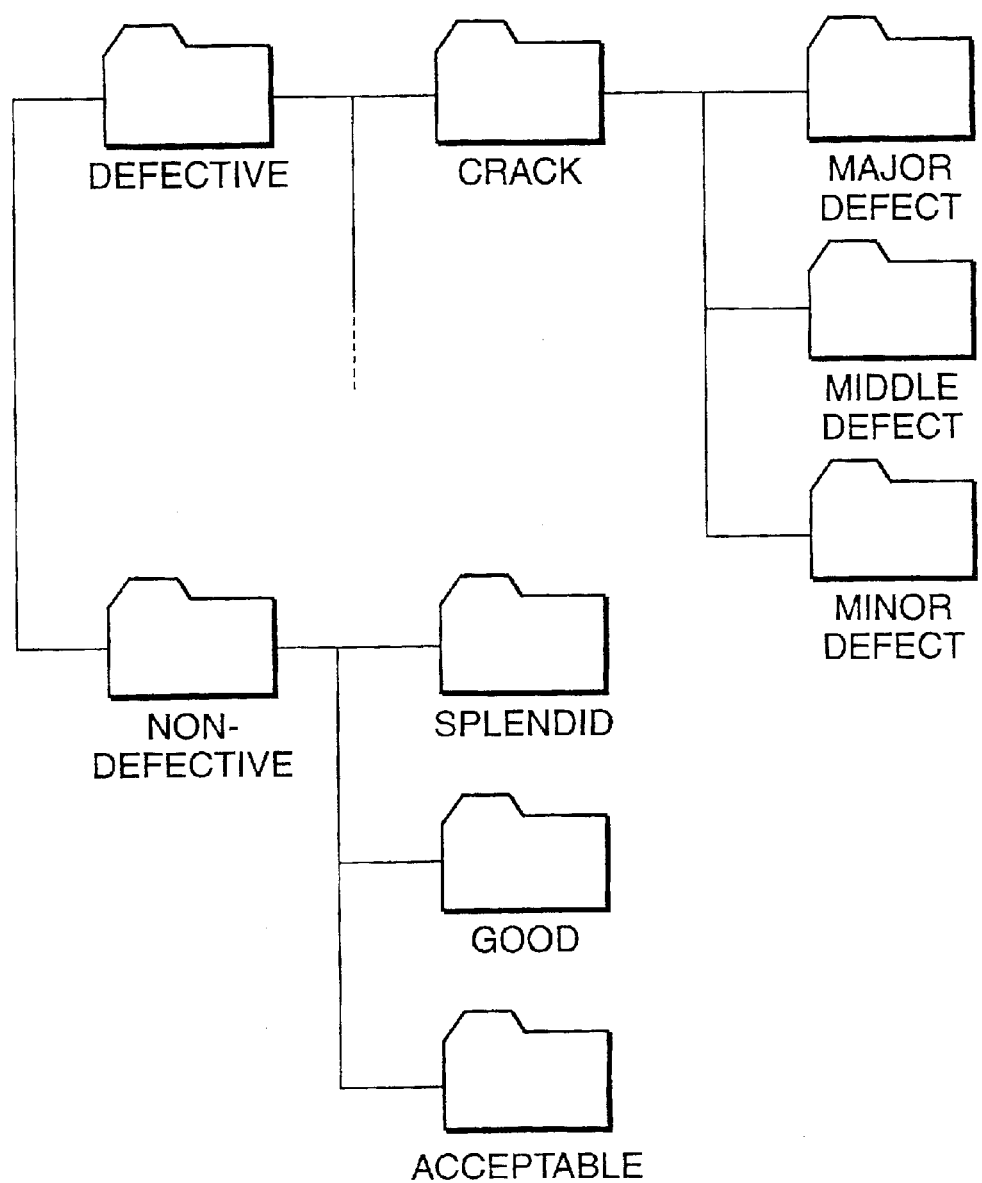
FIG. 6 is a block diagram for showing an example of folders into which image data of defective units and non-defective units are sorted in the first embodiment.

FIG. 6 shows an example of the sorting of the image data of the defective units and non-defective units. In this example, the image data are further sorted corresponding to the degree of defects into the folders named "MAJOR DEFECT", "MIDDLE DEFECT", "MINOR DEFECT", "ACCEPTABLE", "GOOD" and "SPLENDID". The image data sorted into the folder of acceptable has some defects but it is acceptable to be shipped. The image data sorted into the folder of good has a little defect but the defect is no problem. The image data sorted into the folder of splendid rarely has defect. It is possible to provide a folder named "PERFECT" (not shown in the figure) into which the image data having no defect is sorted. The image data sorted into the folder of major defect, middle defect or minor defect has defects not acceptable.

Figure 7:
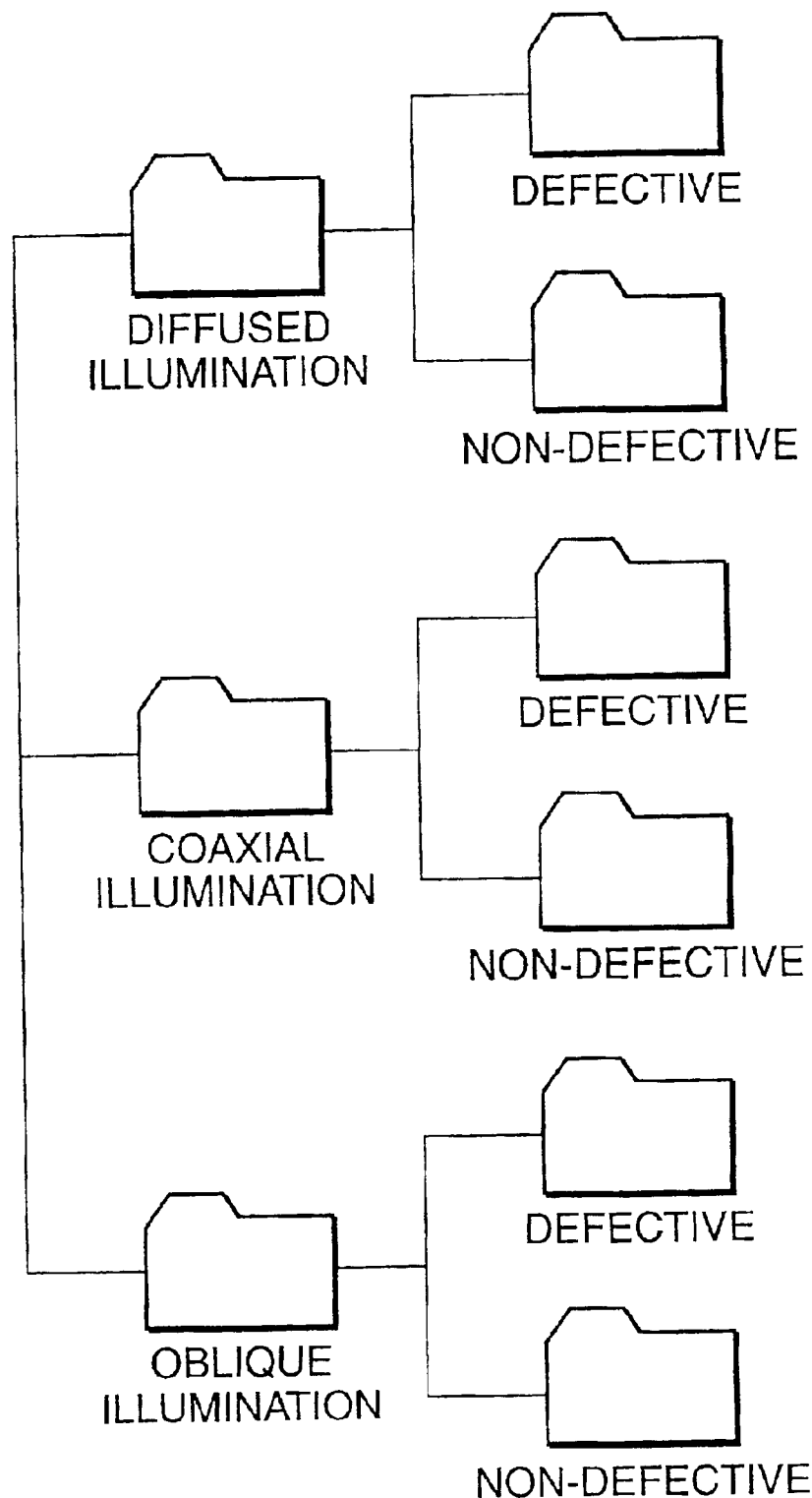
FIG. 7 is a block diagram for showing another example of folders into which image data corresponding to illumination methods in the first embodiment.

FIG. 7 shows another example of sorting of the image data corresponding to the illumination method when the image data of the sample of the defective units and non-defective units of the products are taken. Three folders named "DIFFUSED ILLUMINATION", "COAXIAL ILLUMINATION" and "OBLIQUE ILLUMINATION" are provided. When the same object is illuminated by different illumination methods, the image data taken under the different illumination method will be different at all. Furthermore, there is the most suitable illumination method corresponding to the specification of the products. The folders of defective units and non defective units are provided below the respective folders with respect to the illumination methods.

Figure 8:
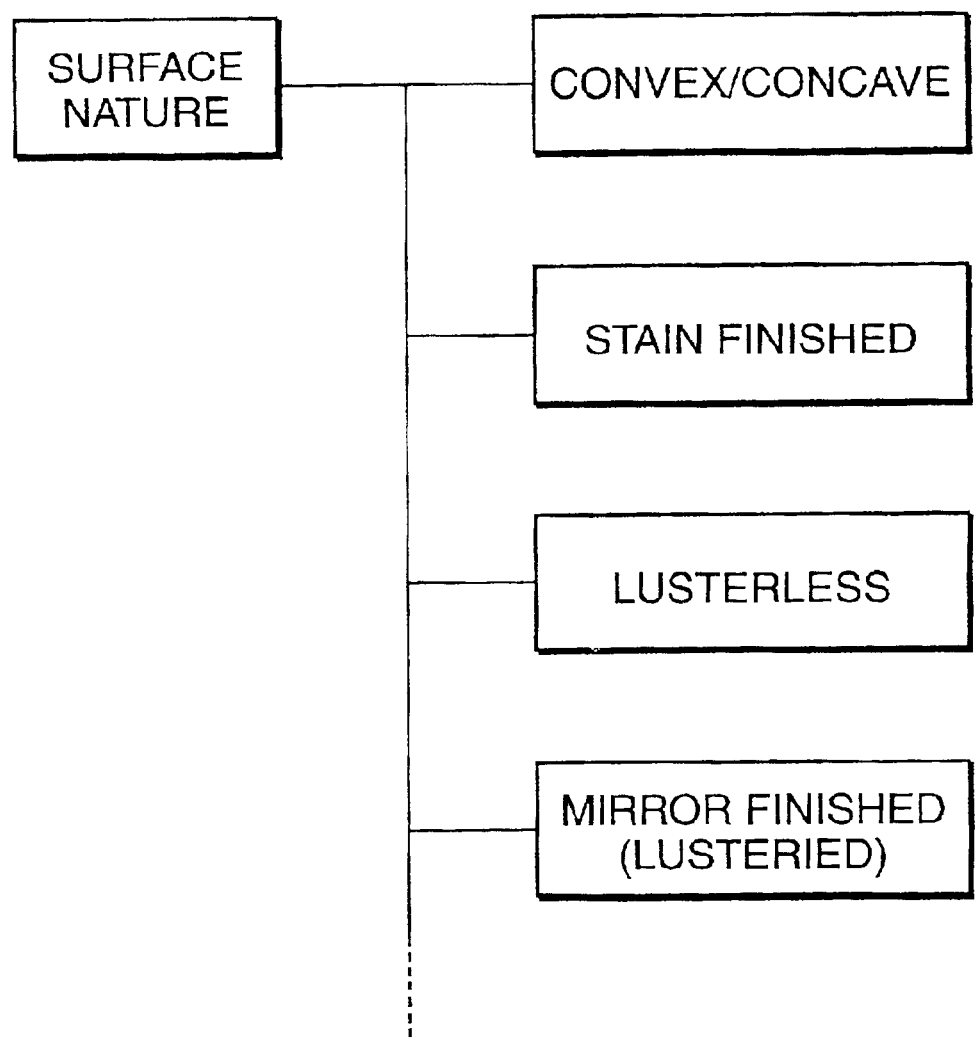
FIG. 8 is a block diagram for showing examples of surface nature or materials of the object to be inspected in the first embodiment.

FIG. 8 shows examples of the surface nature or the materials of the products to be inspected. Generally, a convex and concave structure is formed on the surface of the product. When the convex and concave structure on the surface of the product is sharp, shadows of the convex and concave structure will be observed according to the illumination method. Alternatively, when the convex and concave structure on the surface of the product is dull, edges of the convex and concave structure cannot be observed according to the illumination method. Thus, the standard flow memory 5 memorizes several kinds of the standard inspection flows and inspection parameters corresponding to the convex and concave structure of the surface of the products. Furthermore, the surface of the product is generally finished such as stain finish, mirror finish or lusterless corresponding to the surface nature or material of the product. The standard flow memory 5 further memorizes several kinds of the standard inspection flows and inspection parameters corresponding to the surface nature or material of the surface of the products.

Figure 9:
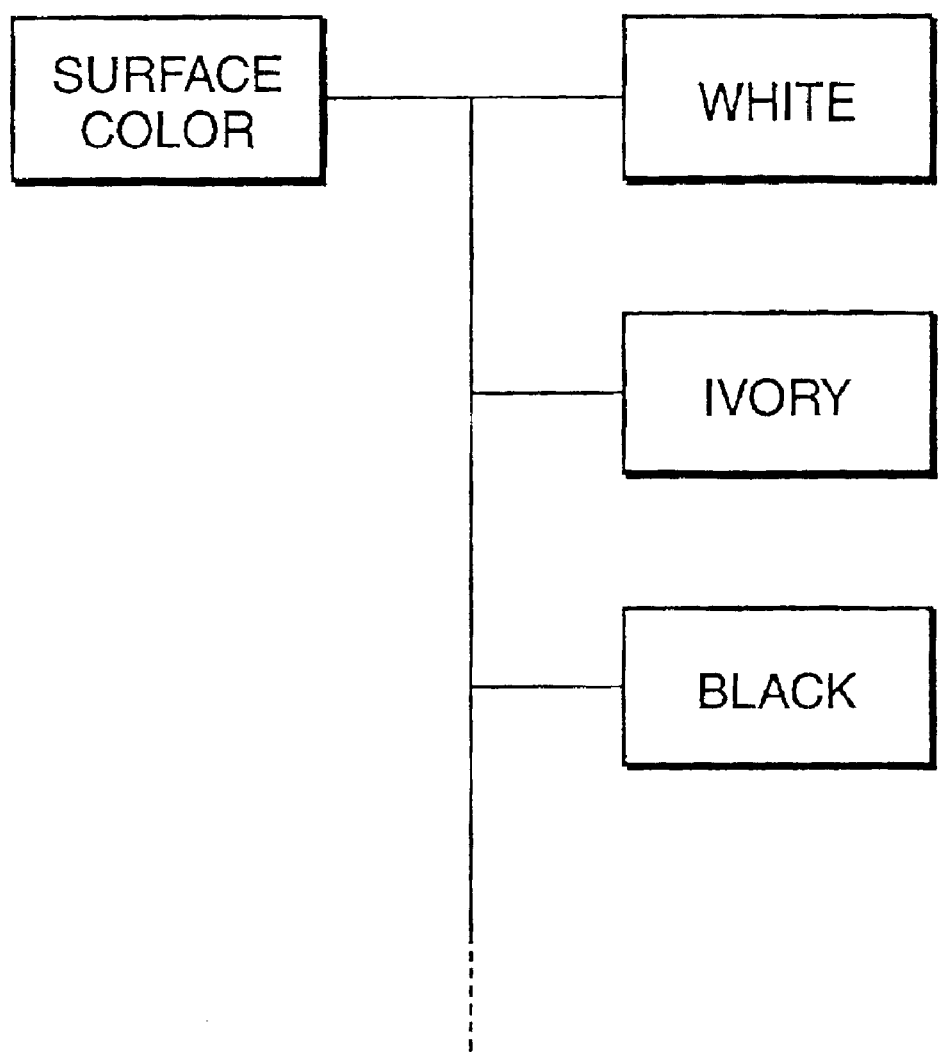
FIG. 9 is a block diagram for showing examples of surface colors of the products to be inspected in the first embodiment.

FIG. 9 shows examples of surface colors of the products to be inspected. Generally, coloring such as white, ivory, black or the like is provided on the surface of the products having the same shape for differentiating the products or for improving the appearance of the products. The image data of the product having the surface color of white is clearly different from that having the surface color of black even though the products have the same shape and the image data are taken under the same condition. Thus, the standard flow memory 5 memorizes several kinds of the standard inspection flows and inspection parameters corresponding to the surface colors of the surface of the products.

Figure 10A:
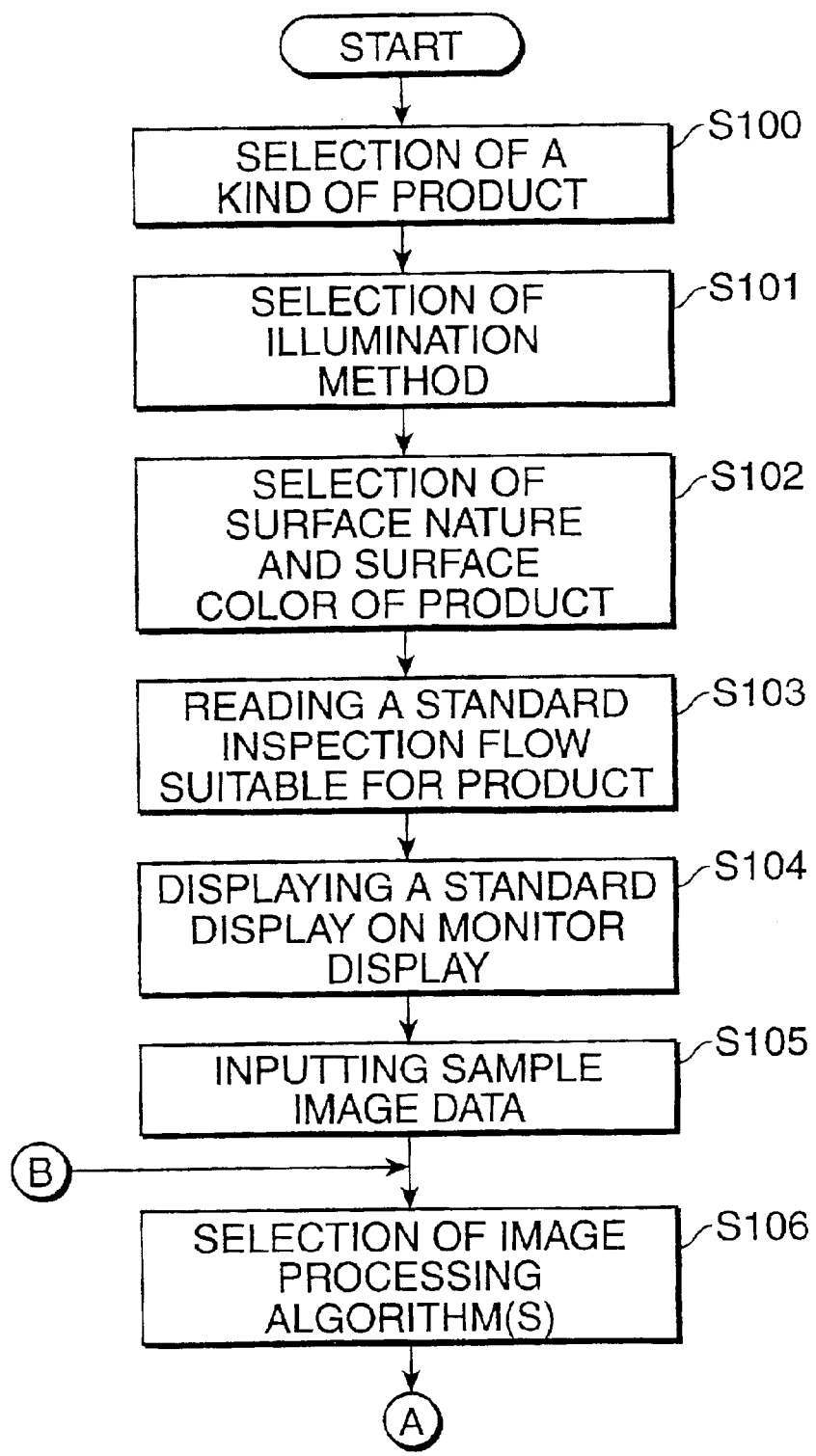
FIGS. 10A and 10B are drawings for showing a flowchart of programming steps of the visual inspection program in the first embodiment.
Figure 10B:
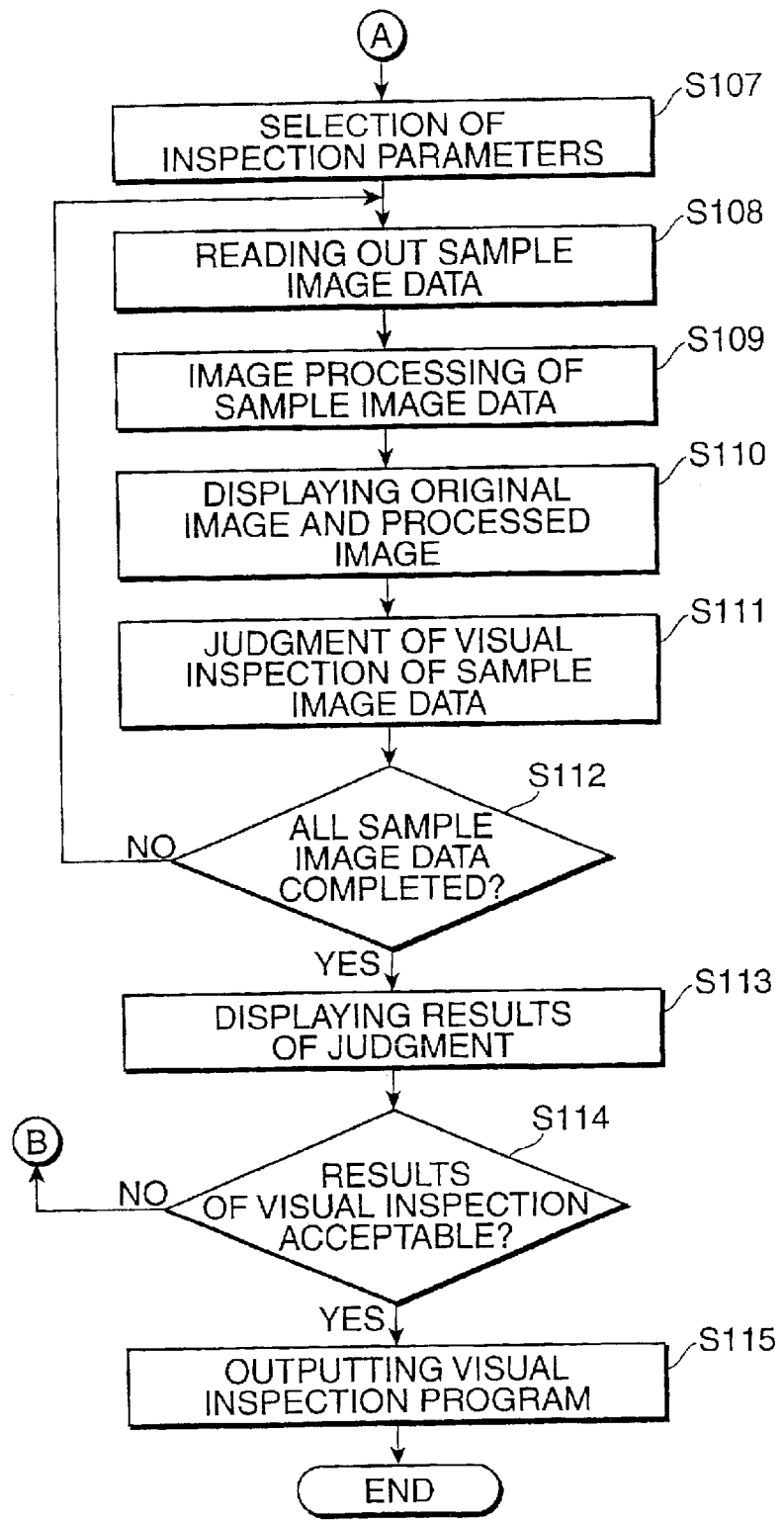

Subsequently, the programming steps of the visual inspection program in the first embodiment is described with reference to a flow chart shown in FIGS. 10A and 10B.

When the program for programming the visual inspection program memorized in the inspection processor 6 is started, the inspection processor 6 displays a predetermined message on the display unit 2 which requires the user to input or to select a kind of product to be inspected (step S100). When the user inputs or selects the switch as the product to be inspected, the inspection processor 6 further requires the user to select the illumination method for illuminating the product to be inspected or to select the image acquisition condition for taking the image data of the product on a manufacturing line (step S101). When the illumination method or image acquisition condition is selected, the inspection processor 6 still further requires the user to select the surface nature and surface color of the switch (step S102).

When the kind of the product, the illumination method, the surface nature and the surface color of the product are inputted or selected by the user, the inspection processor 6 reads out a standard inspection flow suitable for inspecting the product from the standard flow memory 5 (step S103). When the standard inspection flow is read out, the inspection processor 6 displays a standard display, for example, shown in FIG. 4 on the display unit 2 (step S104).

Subsequently, the inspection processor 6 requires the user to input sample image data of the defective units and non defective units of the product (step S105). The sample image data is taken by the image acquisition unit 7 at the time or prior to the programming of the visual inspection program. When the sample image data is inputted, the inspection processor 6 memorizes the sample image data into the image data memory 3 and further requires the user to select at least one image processing algorithm such as inspection of occurrence of crack, adhesion of extraneous matter, occurrence of chipping, or the like (step S106). When at least one of the algorithm is selected, the inspection processor 6 still further requires the user to select the inspection parameters (step S107). The inspection parameters includes a plurality of setting parameters used in the image processing steps and a plurality of judging parameters used for judging whether the visual inspection result of the product is acceptable or not. The setting parameters are, for example, a region to be inspected, and levels of the image processing such as the filtering of the image data, the binary processing and the differential processing.

Figure 11A:
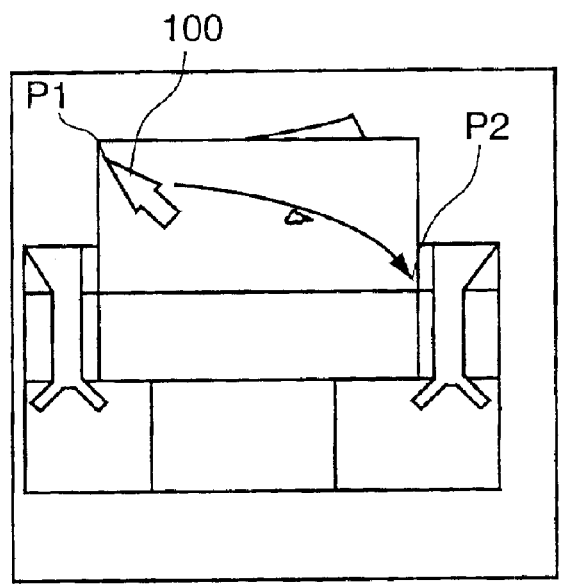
FIGS. 11A and 11B are drawings for showing images of a product displayed on the display unit of the programming apparatus in the first embodiment by which a region to be inspected on a surface of the product can be selected.
Figure 11B:
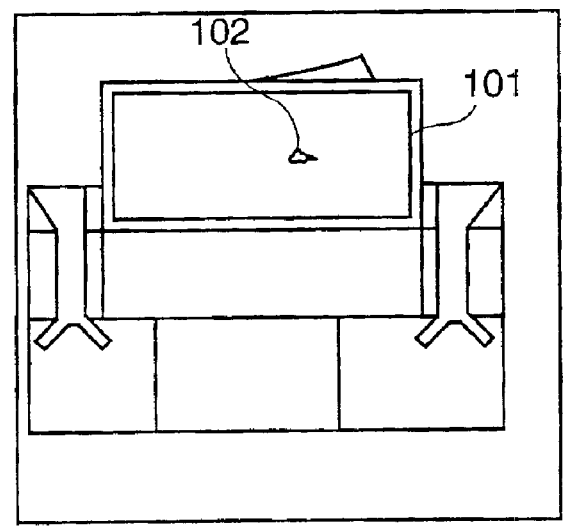

An example for setting the parameter of the region to be inspected is described with reference to FIGS. 11A and 11B which show side views of the product such as the switch to be inspected. In FIG. 11A, a pointer 100 having an arrow shape is moved to a position P1, for example, disposed in the vicinity of the upper left end of the side face of the switch by operating the mouse 12 of the input unit 1. While a switch button of the mouse 12 is switched on, the pointer 100 is moved to a position P2 disposed in the vicinity of the lower right end of the side face of the switch. When the switch button of the mouse 12 is switched off, a rectangular region 101 to be inspected is selected. In the region 101, an extraneous matter 102 which is the cause of the defect is included. The shape of the region to be inspected, however, is not restricted by the rectangle. It is possible to select an optional shape such as a circle, an ellipse, a polygon, or the like suitable for inspecting the product.

When the inspection parameters are selected, a provisional visual inspection parameter is programmed. Thus, the inspection processor 6 starts to execute the provisional visual inspection program. The inspection processor 6 reads out the sample image data of the defective units and the non-defective units of the product serially from the image data memory 3 (step S108). The inspection processor 6 executes the image processing of the sample image data by following the provisional visual inspection program (step S109). When the image processing of the sample image data is completed, the inspection processor 6 displays an original image using the original image data and a processed image data using the processed image data on the display unit 2 (step S110).

Examples of the original image and the processed image displayed on the display unit 2 are shown in FIG. 12. As shown in FIG. 12, the original image and the processed image are displayed on the same monitor display of the display unit at the same time. The original image is disposed at the left side, and the processed image is disposed at the right hand. The extraneous matter 102A in the original image is blurred, but the extraneous matter 102B in the processed image is cleared. Displays of predetermined information data 103 and 104 are superimposed on the original image and the processed image. The information data 103 with respect to the original image includes a file name such as "NG1", a name of product such as "switch", a kind of the product such as "SW1", a cause of the defects such as "extraneous matter" and a rank of the defect such as "major defect". The pointer 100 is further displayed on the processed image for designating the portion of the defect such as the extraneous matter 103B. The information data 104 with respect to the processed image includes a result of the inspection such as "NG", an area of the portion of the defect and the land number of the defects.

Subsequently, the inspection processor 6 executes the judgment of the visual inspection whether the appearance of the product has a unacceptable defect or not (step S111). The inspection processor 6 repeats the steps S108 to S111 until the judgments with respect to all the sample image data are completed (step S112).

When the judgments with respect to all the sample image data are completed, the inspection processor 6 displays the results of the judgment on the display unit 2 (step S113). The user judges whether the results of the judgments of the visual inspection of the sample image data of the product can be acceptable or not (step S114).

Hereupon, when the provisional visual inspection program is properly programmed, the sample image data of the defective units of the product are judged to be unacceptable, and the sample image data of the non-defective units are judged to be acceptable. On the other hand, when the provisional visual inspection program is improperly programmed, the sample image data of the defective units of the product are judged to be acceptable, or the sample image data of the non-defective units are judged to be unacceptable. Thus, when the results of the visual inspection of the sample image data are not acceptable, the user inputs a predetermined command such as "NO" by using the input unit 1, and the inspection processor 6 returns to the step S106 for re-requiring the user to select the image processing algorithm and the inspection parameters again. The steps S106 to S113 will be repeated until the results of the visual inspection of the sample image data becomes acceptable.

When the results of the visual inspection of the sample image data are acceptable, the user inputs a predetermined command such as "YES" by using the input unit 1, and the inspection processor 6 outputs the provisional visual inspection program configured by the standard inspection flow and the selected image processing algorithms and the inspection parameters to the output unit 8 as a final visual inspection program. The output unit 8 records the visual inspection program into a recording medium such as the CD-R, the MO disc, or the like (step S114). When the visual inspection program is outputted, the inspection processor 6 completes the program for programming the image inspection program.

In the above-mentioned flowchart, the position of the step for inputting the sample image data is not restricted by the description. It is possible to input the sample image data at any time when the user wishes until the provisional visual inspection program is started. The same rule applies correspondingly to the following flowcharts.

As mentioned above, the user unaccustomed to the programming language and/or image processing can easily program the visual inspection program suitable for the product to be inspected by using the programming apparatus in the first embodiment.

Figure 13B:
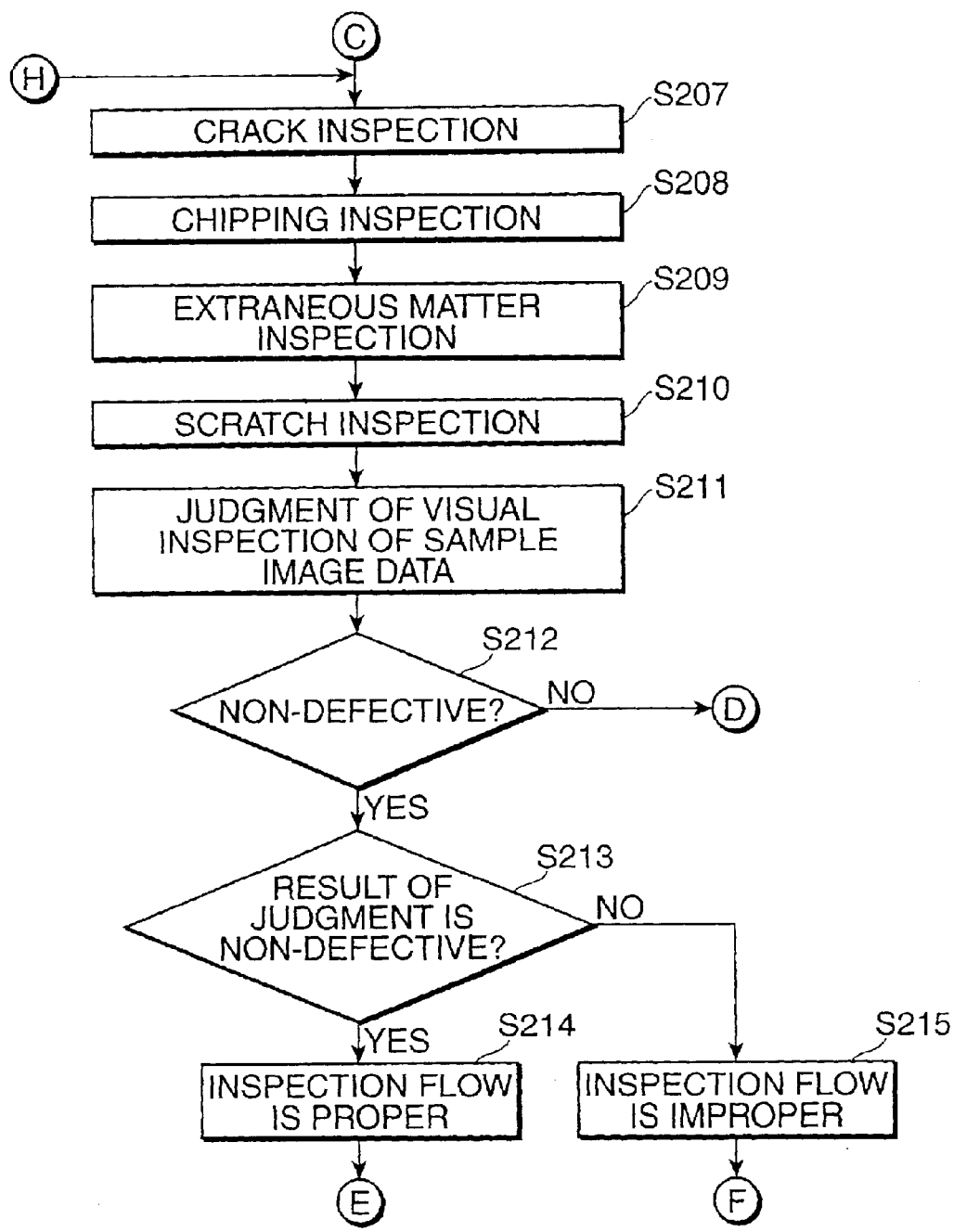
Figure 13C:
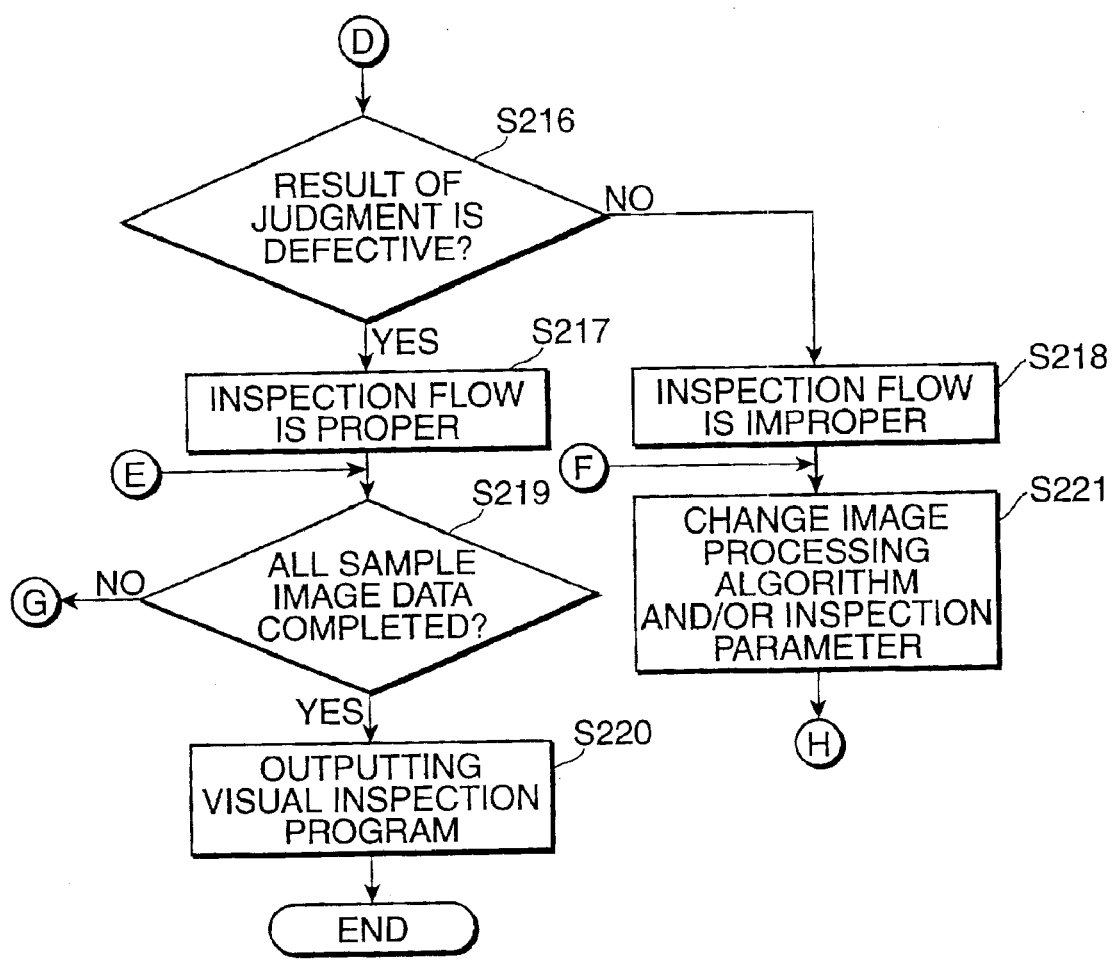

A first modification of the programming steps of the visual inspection program in the first embodiment is described with reference to a flow chart shown in FIGS. 13A to 13C. In the following modifications which will be described below, the steps for displaying the standard display on the display unit, for selecting the illumination method, and for selecting the surface nature and the surface color of the product are omitted.

For example, when the product to be inspected is the switch, it is considered that the defects of the switch are caused by the occurrence of the crack, scratch, chipping or the adhesion of extraneous matters. In the first modification, the inspection items or the image processing algorithms, the standard inspection flow and the inspection parameters, or the combination of them, which are recommended by the expert of the image processing, are previously programmed, and automatically read out from the algorithm memory 4 and the standard flow memory 5, when the user inputs or selects the kind of the product to be inspected.

When the program for programming the visual inspection program memorized in the inspection processor 6 is started, the inspection processor 6 displays a predetermined message on the display unit 2 which requires the user to input or to select the kind of product to be inspected (step S200). When the user selects the switch as the product to be inspected, the inspection processor 6 selects a standard inspection flow from the standard flow memory 5, at least one of the image processing algorithm and the inspection parameters from the algorithm memory 4 which are suitable for inspecting the product and recommended by the expert (step S201).

When the standard inspection flow and so on are selected, the inspection processor 6 requires the user to input sample image data of the defective units and non defective units of the switch (step S202). When the sample image data are inputted, the inspection processor 6 memorizes the sample image data into the image data memory 3. Subsequently, the inspection processor 6 starts the visual inspection by following a provisional visual inspection program configured by the selected standard inspection flow, the image processing algorithms and the inspection parameters (step S203).

The inspection processor 6 reads out the sample image data of the defective units and the non-defective units of the product serially from the image data memory 3 (step S204). When one of the sample image data is read out, the inspection processor 6 executes the detection and location of the edges of the image using the sample image data in the horizontal direction by following the provisional visual inspection program (step S205). Subsequently, the inspection processor 6 executes the detection and location of the edges of the image in the vertical direction (step S206).

When the locations of the edges of the image in the horizontal and vertical directions are completed, the inspection processor 6 executes the inspection of the occurrence of the crack (step S207), the occurrence of the chipping (step S208), the adhesion of the extraneous matters (step S209) and the occurrence of the scratch (step S210) with respect to each surface of the product.

When the above-mentioned inspections are completed with respect to each sample image data, the inspection processor 6 executes the judgment of the visual inspection whether the appearance of the product has a defect unacceptable or not (step S211). When the judgment of the visual inspection of the sample image is completed, the inspection processor 6 judges whether the sample image data executed by the above-mentioned inspections is non-defective or defective (step S212).

When the sample image data is non-defective, the inspection processor 6 further judges whether the result of the judgment of the visual inspection is non-defective or not (step S213). When the judgment of the visual inspection is non-defective, the result of the judgment coincides with the nature of the sample image data, so that the inspection processor 6 judges the provisional visual inspection program configured by standard inspection flow, the image processing algorithms and the inspection parameters is proper (or good) visually for inspecting the switch (step S214). Alternatively, when the judgment of the visual inspection is defective, the result of the judgment does not coincide with the nature of the sample image data, so that the non-defective unit will be lost by miss-judgment of the visual inspection. Thus, the inspection processor 6 judges the provisional visual inspection program is improper (no good) visually for inspecting the switch (step S215).

When the sample image data is defective in the step S212, the inspection processor 6 further judges whether the result of the judgment of the visual inspection is defective or not (step S216). When the judgment of the visual inspection is defective, the result of the judgment coincides with the nature of the sample image data, so that the inspection processor 6 judges the provisional visual inspection program is proper (good) visually for inspecting the switch (step S217). Alternatively, when the judgment of the visual inspection is non-defective, the result of the judgment does not coincide with the nature of the sample image data, so that the defective unit will be included in the non-defective units by miss-judgment of the visual inspection. Thus, the inspection processor 6 judges the provisional visual inspection program is improper (no good) visually for inspecting the switch (step S218).

When the provisional visual inspection program is judged proper in the steps S214 and S217, the inspection processor 6 judges whether the visual inspections with respect to all the sample image data are completed or not (step S219). When all the sample data are not inspected yet, the inspection processor 6 returns to the step S204 for repeating the steps S204 to S219 and S221 (described below) with respect to the next sample image data. Alternatively, when all the sample data are inspected, the inspection processor 6 outputs the provisional visual inspection program configured by the standard inspection flow, the selected image processing algorithms and the inspection parameters to a memory of the visual inspection apparatus or records the provisional visual inspection program into a recording medium such as a CD-R, an MO disc, or the like as the visual inspection program (step S220). When the visual inspection program is outputted, the inspection processor 6 completes the program for programming the image inspection program.

When the provisional visual inspection program is judged improper in the steps S215 and S218, the inspection processor 6 requires the user to change at least one image processing algorithms and/or at least one inspection parameter (step S221), and returns to the step S207 for repeating the steps S207 to S219 and S221 with respect to the same sample image data.

In the above-mentioned first modification, the combination of the standard inspection flow, the image processing algorithms and the inspection parameters which are recommended by the expert of the image processing is automatically selected when the user inputs or selects the kind of the product to be inspected, so that the user unaccustomed to the programming language and the image processing can easily program the visual inspection program suitable for the specific product to be inspected. Furthermore, the judgment whether the provisional visual inspection program configured by the standard inspection flow, the image processing algorithms and the inspection parameters are proper or improper visually for inspecting the product such as the switch selected by the user is automatically judged by the program for programming the visual inspection program. Thus, the user occasionally participates in the programming processes for programming the visual inspection program suitable for the specific product to be inspected.

Figure 14A:
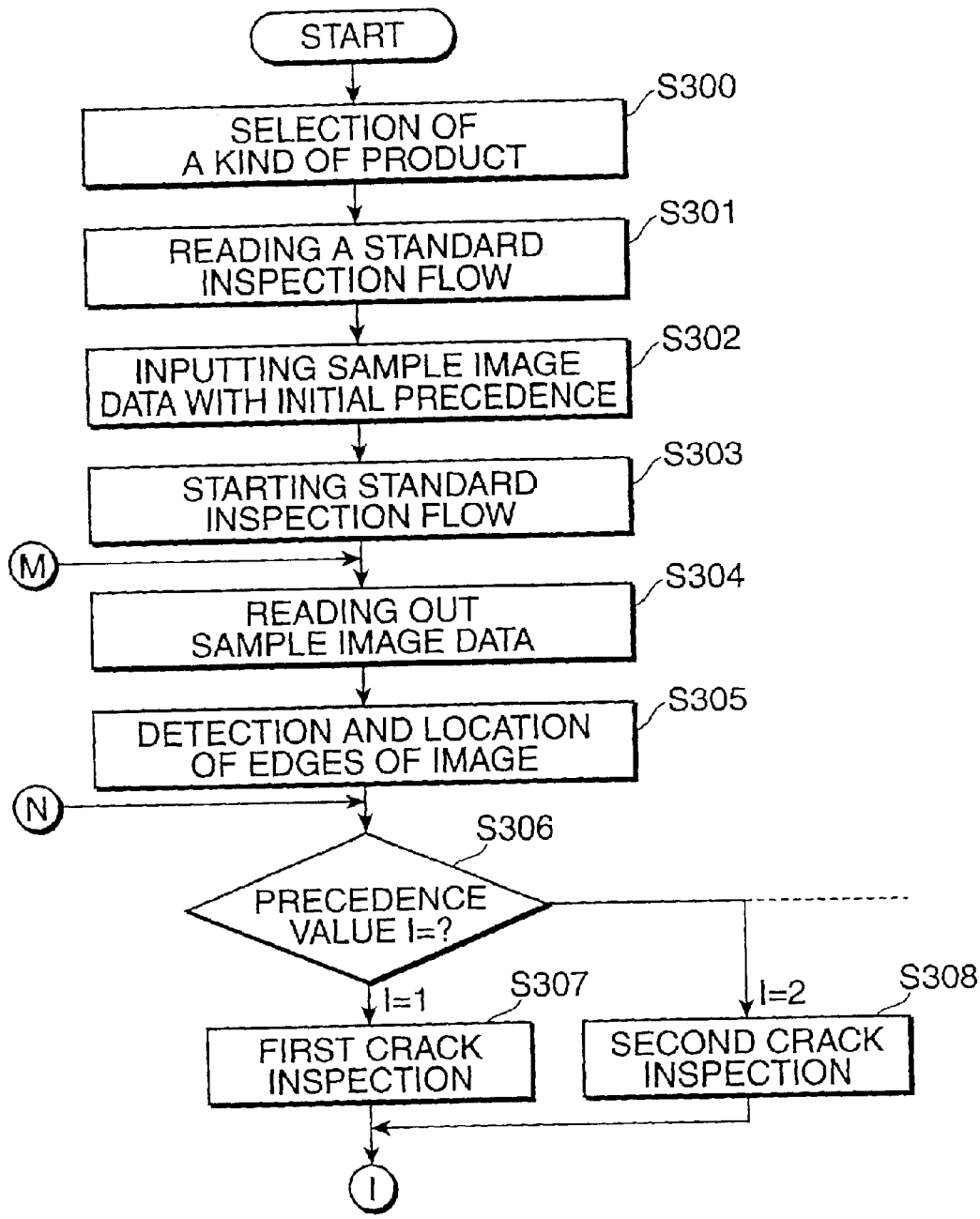
FIGS. 14A to 14C are drawings for showing a flowchart of a second modification of the programming steps of the visual inspection program in the first embodiment.
Figure 14B:
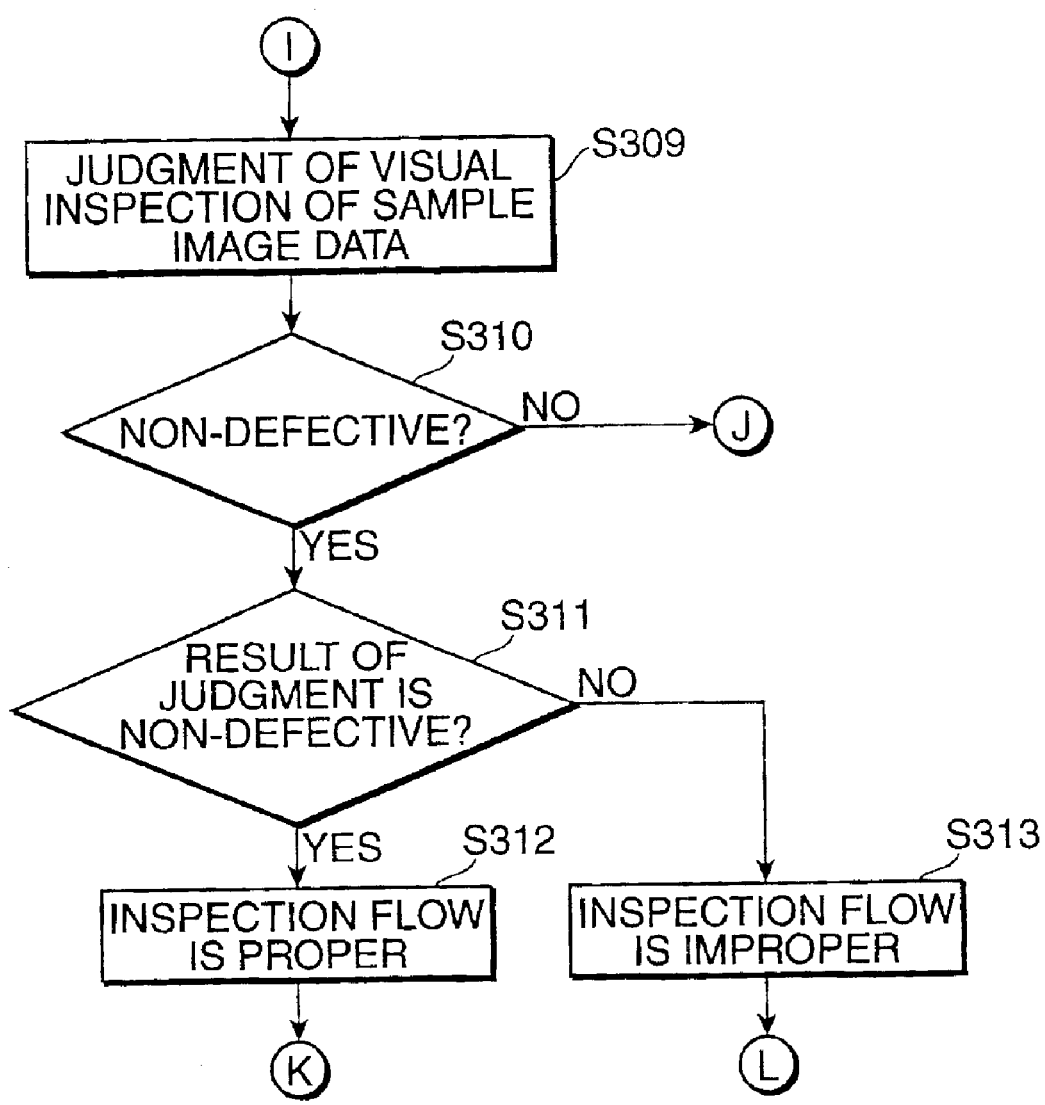
Figure 14C:
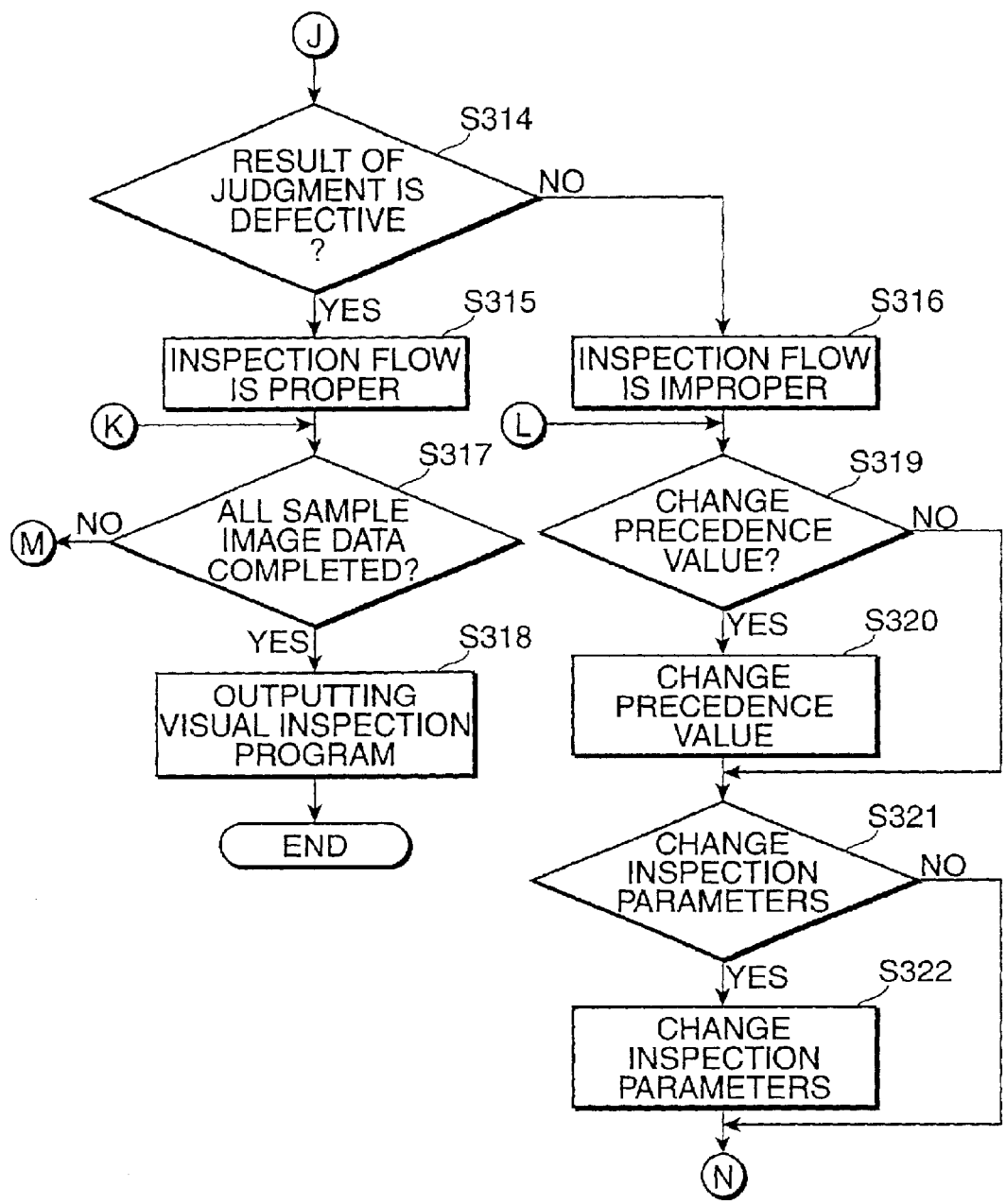

A second modification of the programming steps of the visual inspection program in the first embodiment is described with reference to a flow chart shown in FIGS. 14A to 14C. For simplifying the description of the second modification, only the occurrence of the crack is inspected as the inspection item. In the second modification, a plurality of the image processing algorithms with respect to the same inspection item are prepared, and each image processing algorithm has a precedence value. Furthermore, each sample data used for the visual inspection has an initial value of the precedence.

When the program for programming the visual inspection program memorized in the inspection processor 6 is started, the inspection processor 6 displays a predetermined message on the display unit 2 which requires the user to input or to select the kind of product to be inspected (step S300). When the user inputs or selects the switch as the product to be inspected, the inspection processor 6 selects a standard inspection flow from the standard flow memory 5, at least one of the image processing algorithm and so on (step S301).

When the standard inspection flow and so on are selected, the inspection processor 6 requires the user to input sample image data of the defective units and non-defective units of the product and the initial precedence with respect to each sample image data (step S302). When the sample image data and the initial precedence values are inputted, the inspection processor 6 memorizes the sample image data and the initial precedence values into the image data memory 3. Subsequently, the inspection processor 6 starts a provisional visual inspection program configured by the standard inspection flow and so on for inspecting the sample image data (step S303).

The inspection processor 6 reads out the sample image data of the defective units and the non-defective units of the product serially from the image data memory 3 (step S304). When one of the sample image data is read out, the inspection processor 6 executes the detection and location of the edges of the image using the sample image data in the horizontal and vertical directions (step S305).

When the locations of the edges of the image in the horizontal and vertical directions are completed, the inspection processor 6 reads out the initial precedence value "I" of the image data (step S306). When the initial precedence value I=1, the inspection processor 6 reads out and executes the image processing algorithm such as a first crack inspection having the precedence value I=1 (step S307). When the initial precedence value I=2, the inspection processor 6 reads out and executes the image processing algorithm such as a second crack inspection having the precedence value I=2 (step S308).

When the above-mentioned crack inspection is completed, the inspection processor 6 executes the judgment of the visual inspection whether the appearance of the product has a defect unacceptable or not (step S309). When the judgment of the visual inspection of the sample image is completed, the inspection processor 6 judges whether the sample image data executed by the above-mentioned inspections is non-defective or defective (step S310).

When the sample image data is non-defective, the inspection processor 6 further judges whether the result of the judgment of the visual inspection is non-defective or not (step S311). When the judgment of the visual inspection is non-defective, the result of the judgment coincides with the nature of the sample image data and the precedence value of the sample image data is proper, so that the inspection processor 6 judges the provisional visual inspection program configured by the standard inspection flow, the image processing algorithms and the inspection parameters is proper (good) visually for inspecting the product (step S312). Alternatively, when the judgment of the visual inspection is defective, the result of the judgment does not coincide with the nature of the sample image data, so that the non-defective unit will be lost by miss-judgment of the visual inspection due to the improper precedence value of the sample image data. Thus, the inspection processor 6 judges the provisional visual inspection program is improper (no good) visually for inspecting the product (step S313).

When the sample image data is defective in the step S310, the inspection processor 6 further judges whether the result of the judgment of the visual inspection is defective or not (step S314). When the judgment of the visual inspection is defective, the result of the judgment coincides with the nature of the sample image data, so that the inspection processor 6 judges the provisional visual inspection program is proper (good) visually for inspecting the product (step S315). Alternatively, when the judgment of the visual inspection is non-defective, the result of the judgment does not coincide with the nature of the sample image data, so that the defective unit will be included in the non-defective units by miss-judgment of the visual inspection. Thus, the inspection processor 6 judges the provisional visual inspection program is improper (no good) visually for inspecting the product (step S316).

When the standard inspection flow is judged proper in the steps S312 and S315, the inspection processor 6 judges whether the visual inspections with respect to all the sample image data are completed or not (step S317). When all the sample data are not inspected yet, the inspection processor 6 returns to the step S304 for repeating the steps S304 to S317 and S319 to S322 (described below) with respect to the next sample image data. Alternatively, when all the sample data are inspected, the inspection processor 6 outputs the provisional visual inspection program configured by the standard inspection flow, the selected image processing algorithms and the inspection parameters to a memory of the visual inspection apparatus or records the visual inspection program into a recording medium such as a CD-R, an MO disc, or the like as a final visual inspection program (step S318). When the visual inspection program is outputted, the inspection processor 6 completes the program for programming the image inspection program.

When the provisional visual inspection program is judged improper in the steps S313 and S316, the inspection processor 6 inquires the user to change the precedence value or not (step S319). When the user wishes to change the precedence value, the inspection processor 6 requires the user to change the precedence value of the sample image data (step S320). When the user does not wish to change the precedence value (NO in the step S319) or when the precedence value is changed in the step S320, the inspection processor 6 further inquires the user to change the inspection parameters (step S321). When the user wishes to change the inspection parameters, the inspection processor 6 requires the user to change the inspection parameters (step S322). When the user does not wish to change the inspection parameters (NO in the step S321) or when the inspection parameters are changed in the step S322, the inspection processor 6 returns to the step S306 for repeating the steps S306 to S317 and S319 to S322 with respect to the same sample image data.

In the above-mentioned second modification, the precedence is set to the image processing algorithms included in the same criteria, and the user can select the most suitable image processing algorithm visually for inspecting the product to be inspected.

In the second modification, the image processing algorithms have the precedence. FIG. 15 shows another modification that the inspection parameters have the precedence. FIG. 15 is a table for showing the example of the inspection parameters, which is displayed on the display unit 2. The precedence of each parameter shows the degree that the variation of the values of the parameter effects the result of the image processing of the image data. In the table shown in FIG. 15, the symbol "+" designates that the value of the parameter is increased from the current value, and the symbol "−" designates that the value of the parameter is decreased from the current value.

In this example, when a result of a visual inspection of a sample image data inspected by a standard inspection flow with previously selected image processing algorithms and inspection parameters is not acceptable, the parameter having the precedence value "1" such as the threshold value of the edge detection will be varied from the initial value "50" by the predetermined width "52 in both of increasing and decreasing directions between the limitation values "2" to "100". The threshold value of the edge detection will be varied as 50→55→45→60→40→65→35 . . . . Similarly, the threshold value of the edge extension will be varied as 30→35→25→40→20→45→15 . . . .

By such a configuration, the user can easily change the inspection parameters by following the precedence, when the provisional visual inspection program is judged improper.

Figure 16A:
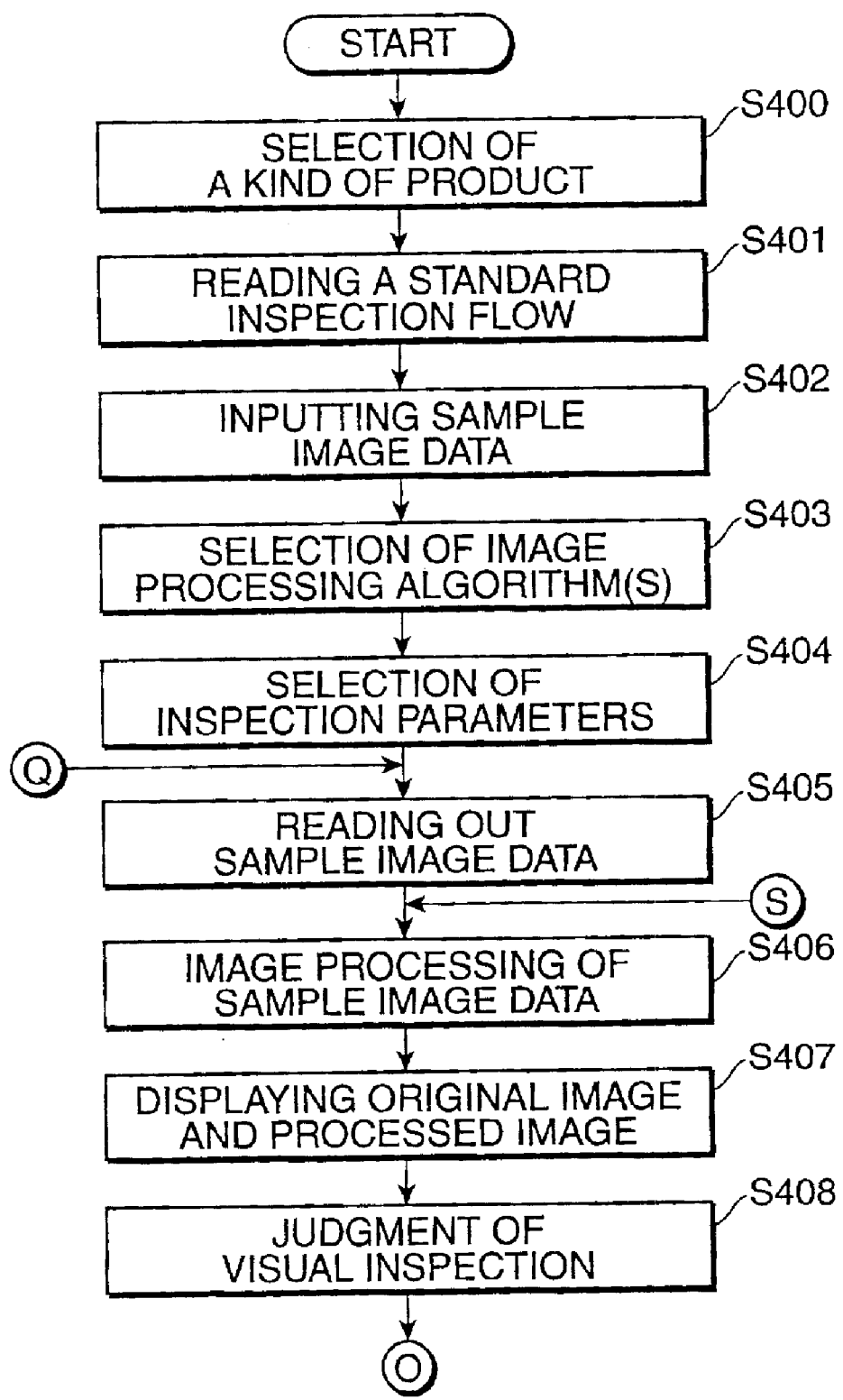
FIGS. 16A to 16C are drawings for showing a flowchart of a third modification of the programming steps of the visual inspection program in the first embodiment.
Figure 16B:
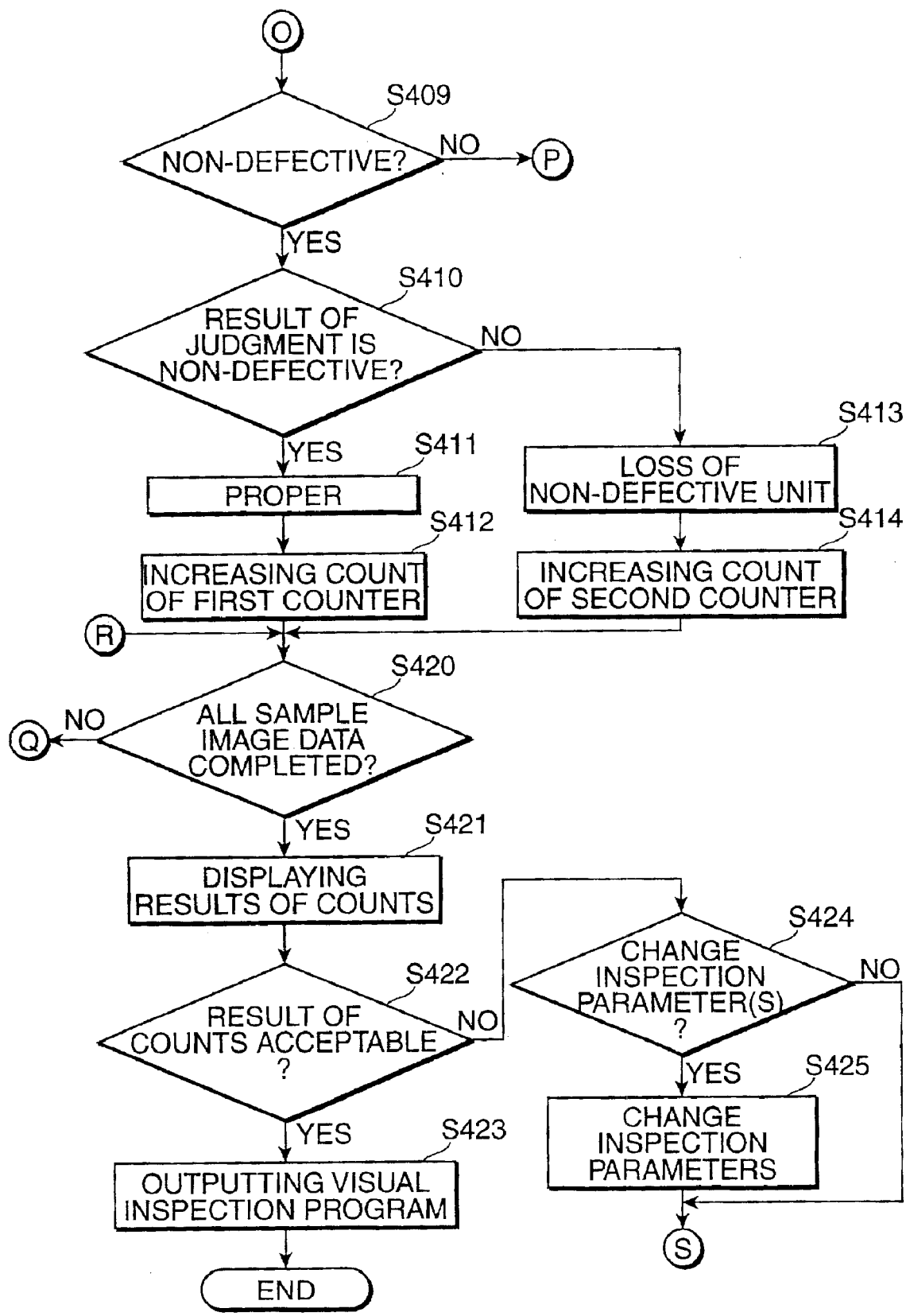
Figure 16C:
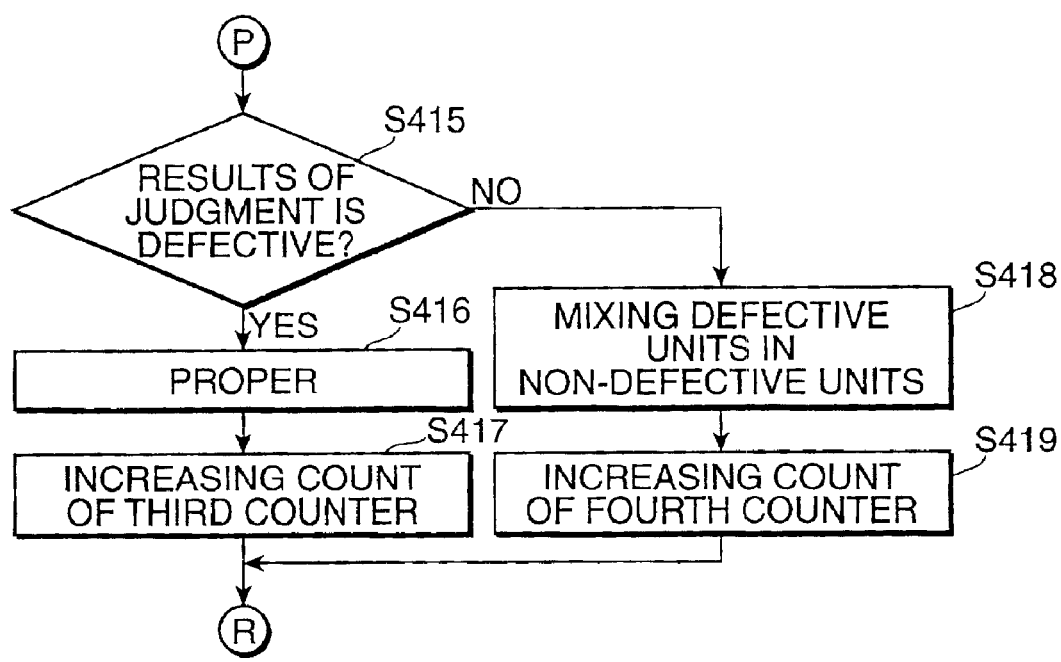

A third modification of the programming steps of the visual inspection program in the first embodiment is described with reference to a flow chart shown in FIGS. 16A to 16C. In the third modification, the provisional visual inspection program configured by the standard inspection flow, the image processing algorithms and the inspection parameters is evaluated by number of occurrence of missjudgment of the visual inspection of the sample image data.

When the program for programming the visual inspection program memorized in the inspection processor 6 is started, the inspection processor 6 displays a predetermined message on the display unit 2 which requires the user to input or to select the kind of product to be inspected (step S400). When the user inputs or selects the switch as the product to be inspected, the inspection processor 6 selects a standard inspection flow from the standard flow memory 5 (step S401).

When the standard inspection flow is selected, the inspection processor 6 requires the user to input sample image data of the defective units and non-defective units of the product (step S402). When the sample image data are inputted, the inspection processor 6 memorizes the sample image data into the image data memory 3. Subsequently, the inspection processor 6 requires the user to select at lest one image processing algorithm (step S403), and to select the inspection parameters (step S404).

Subsequently, the inspection processor 6 reads out the sample image data of the defective units and the non-defective units of the product serially from the image data memory 3 (step S405). When one of the sample image data is read out, the inspection processor 6 executes the provisional visual inspection program such as the detection and location of the edges of the image using the sample image data in the horizontal and vertical directions, the filtering process, and so on (step S406).

When the image processing is completed, the inspection processor 6 displays the original image and the processed image on the display unit 2 (step S407). Simultaneously, the inspection processor 6 executes the judgment of the visual inspection whether the appearance of the product has a defect unacceptable or not (step S408). When the judgment of the visual inspection of the sample image is completed, the inspection processor 6 judges whether the sample image data executed by the above-mentioned inspections is non-defective or defective (step S409).

When the sample image data is non-defective, the inspection processor 6 further judges whether the result of the judgment of the visual inspection is non-defective or not (step S410). When the judgment of the visual inspection is non-defective, the result of the judgment coincides with the nature of the sample image data, so that the inspection processor 6 judges the provisional visual inspection program configured by the standard inspection flow, the image processing algorithms and the inspection parameters is proper (good) visually for inspecting the product (step S411). Furthermore, the inspection processor 6 increases a count of a first counter by one (step S412). Alternatively, when the judgment of the visual inspection is defective, the result of the judgment does not coincide with the nature of the sample image data, so that the non-defective unit will be lost by miss-judgment of the visual inspection (step S413). The inspection processor 6 increases a count of a second counter by one (step S414).

When the sample image data is defective in the step S409, the inspection processor 6 further judges whether the result of the judgment of the visual inspection is defective or not (step S415). When the judgment of the visual inspection is defective, the result of the judgment coincides with the nature of the sample image data, so that the inspection processor 6 judges whether the provisional visual inspection program is proper (good) visually for inspecting the product (step S416). The inspection processor 6 increases a count of a third counter by one (step S417). Alternatively, when the judgment of the visual inspection is non-defective, the result of the judgment does not coincide with the nature of the sample image data, so that the defective unit will be mixed in the non-defective units by miss-judgment of the visual inspection (step S418). The inspection processor 6 increases a count of a fourth counter by one (step S419).

When the count of any of the first to fourth counters is increased, the inspection processor 6 judges whether the visual inspections with respect to all the sample image data are completed or not (step S420). When all the sample data are not inspected yet, the inspection processor 6 returns to the step S405 for repeating the steps S405 to S420 with respect to the next sample image data. Alternatively, when all the sample data are inspected, the inspection processor 6 displays the counts of the first to fourth counters in a table on the display unit 2 (step S421). Simultaneously, the inspection processor 6 requires the user whether the results of the counts of the first to fourth counters that is the result of the visual inspection of the sample image data is acceptable or not (step S422).

When the user judges that the result of the visual inspection of the sample image data is acceptable, the user inputs a predetermined command such as "YES" by using the input unit 1. The inspection processor 6 outputs the provisional visual inspection program configured by the standard inspection flow, the selected image processing algorithms and the inspection parameters to a memory of the visual inspection apparatus or records the visual inspection program into a recording medium such as a CD-R, an MO disc, or the like as the visual inspection program (step S423). When the visual inspection program is outputted, the inspection processor 6 completes the program for programming the image inspection program.

Alternatively, when the user judges that the result of the visual inspection of the sample image data is not acceptable, the user inputs a predetermined command such as "NO" by using the input unit 1. The inspection processor 6 inquires the user to change at least one inspection parameter (step S424). When the user wishes to change the inspection parameter, the inspection processor 6 displays a predetermined message for requesting the user to change the inspection parameters, and the inspection processor 6 changes the inspection parameter responding to the instruction of the user (step S425). Subsequently, the inspection processor 6 returns to the step S406 for repeating the steps S406 to S420 with respect to the same sample image data.

In the above-mentioned third modification, the user can be judged whether the visual inspection program is acceptable or not by referring to the counts of the counters showing the ratio of the number of the miss-judgment with respect to the number of the proper judgment. For example, even when the miss-judgment for judging the non-defective units as the defective units occasionally occurs, the visual inspection program is acceptable while the defective units never included in the non-defective units. Alternatively, even when the miss-judgment for judging the defective units as the non-defective units rarely occurs, the visual inspection program is not acceptable while at least one defective unit is included in the non-defective units.

An example of a table of the judgment of the visual inspection of the sample image data and the ratio of the number of the miss-judgment with respect to the number of the proper judgment is shown in FIG. 17.

In FIG. 17, the upper half portion of the table shows the inspection result that seven non-defective sample image data are inspected by image processing algorithms for inspecting the occurrence of the crack, the occurrence of the chipping, the adhesion of the extraneous matter and the occurrence of the scratch, and the lower half portion of the table shows the inspection result that four defective sample image data caused by the occurrence of the crack and three defective sample image data caused by the adhesion of the extraneous matter are inspected by the same image processing algorithms. The boxes disposed at right hand of the boxes named "CRACK", "CHIPPING", "EXTRANEOUS MATTER" and "SCRATCH" designate the inspection results of the sample image data by using the image processing algorithms suitable for inspecting the named defects.

In the upper half portion of the table with respect to non-defective sample image data, the symbol "o" designates that the non-defective sample image data are judged non-defective, and the symbol "X" designates that the non-defective sample image data is judged defective. In the lower half portion of the table with respect to the defective sample image data, the symbol "o" designates that the defective sample image data are judged defective, and the symbol "X" designates that the defective sample image data is judged non-defective.

For example, the symbol "X" in the box B1 shows that the processed image of the third non-defective sample image data after the image processing by the image processing algorithm suitable for the inspection of the occurrence of the chipping was judges defective. Similarly, the symbol "X" in the box B2 shows that the processed image of the sixth non-defective sample image data after the image processing by the image processing algorithm suitable for the inspection of the occurrence of the scratch was judges defective. As mentioned above, it is acceptable that the non-defective units are occasionally removed from the manufacture line as defective.

On the other hand, the symbol "X" in the box B3 shows that the processed image of the third defective sample image data caused by the occurrence of the crack after the image processing by the image processing algorithm suitable for the inspection of the occurrence of the crack was judges non-defective. Similarly, the symbol "X" in the box B4 shows that the processed image of the second defective sample image data caused by the adhesion of the extraneous matter after the image processing by the image processing algorithm suitable for the inspection of the occurrence of the crack was judges non-defective.

The visual inspection program used in the visual inspection of the sample image data has a problem that the defect caused by the occurrence of the crack cannot be sensed by the image processing algorithm suitable for inspection of the occurrence of the crack. It is necessary to change the inspection algorithm and/or the inspection parameters so as to judge the processed image of the third defective sample image data caused by the occurrence of the crack after the image processing by the image processing algorithm suitable for the inspection of the occurrence of the crack as defective or "○" in the box B3.

Furthermore, it is possible to configure the visual inspection program in a manner so that the original image and the processed image can be displayed on the display unit 2 as shown in FIG. 12, when a desired box, for example, the box B5 is selected by the pointer 100.

In the above-mentioned third embodiment, the inspection processor 6 displays the counts of the first to fourth counters in the table, for example, shown in FIG. 17 on the display unit 2 in the step S421, and requires the user whether the results of the counts of the first to fourth counters that is the result of the visual inspection of the sample image data is acceptable or not in the step S422. It, however, is possible to configure the flowchart in a manner so that target values of the counts of the first to fourth counters are previously set as the inspection parameters; the counts of the first to fourth counters are compared with the target values; when the counts of the first to fourth counters satisfy predetermined conditions, the inspection processor 6 can judge the provisional visual inspection program proper; and when the counts of the first to fourth counters do not satisfy predetermined conditions, the inspection processor 6 changes the inspection parameters by following the precedence until the counts of the first to fourth counters satisfy predetermined conditions. By such a configuration, the visual inspection program can substantially automatically programmed without the selection of the inspection parameters by the user.

Figure 18:
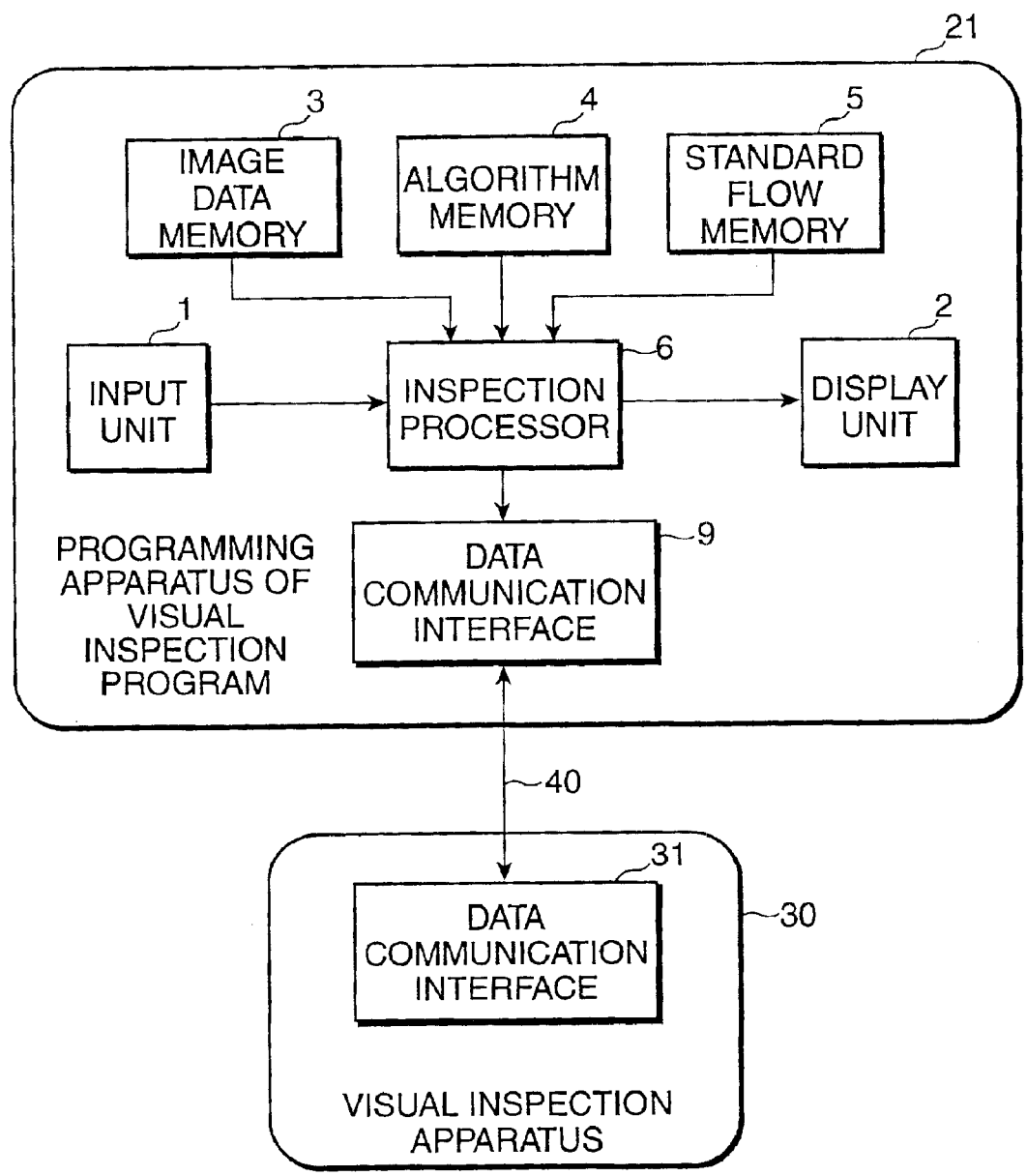
FIG. 18 is a block diagram for showing a system configured by a programming apparatus of a visual inspection program and a visual inspection apparatus in accordance with a second embodiment of the present invention.

A second embodiment of the present invention is described. FIG. 18 shows a block diagram of a system configured by a programming apparatus 21 of the visual inspection program and a visual inspection apparatus 30. In comparison with FIG. 18 and FIG. 1, the programming apparatus 21 in the second embodiment comprises a data communication interface 9 further to the configuration of the programming apparatus 20 in the first embodiment.

The data communication interface 9 is communicated with a data communication inter face 31 of the visual inspection apparatus 30 by a wired or wireless data communication system 40, such as a serial data communication system, a parallel data communication system or a LAN (Local Area Network). The inspection processor 6 further includes a function to output the visual inspection program to the data communication interface 9.

By such a configuration, the visual inspection program programmed by the programming apparatus 21 can be installed into the visual inspection apparatus 30 independently provided from the programming apparatus 21 without using any recording medium. Furthermore, the same programming apparatus 21 can commonly be used for programming the visual inspection programs for a plurality of the visual inspection apparatuses 30.

Alternatively, the user having the visual inspection apparatus 30 but no programming apparatus can use the programming apparatus 21 of the vender of the visual inspection apparatus via the data communication system 40, so that he can obtain the visual inspection program suitable for inspecting the product which he wishes to inspect.

Figure 19:
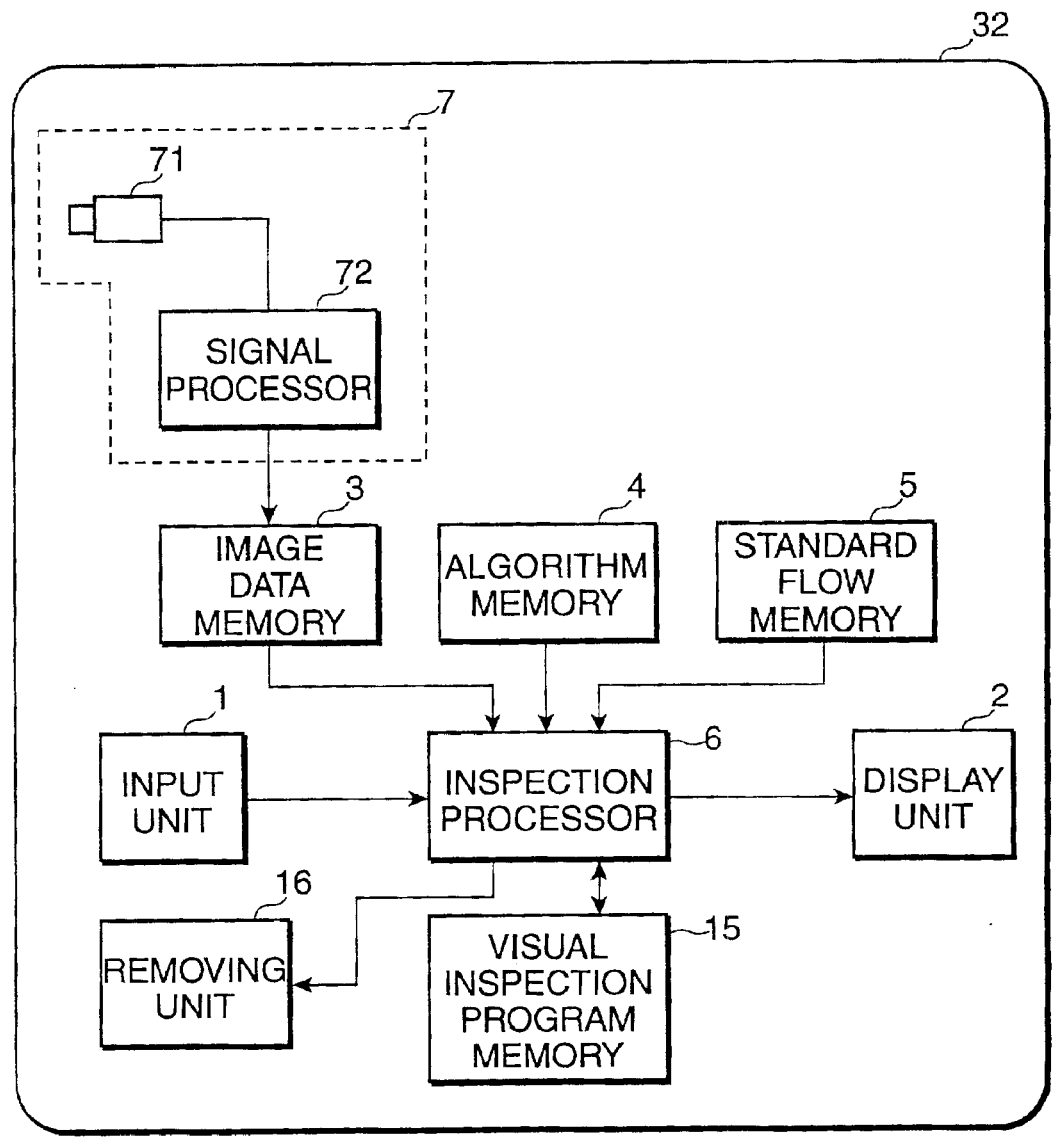
FIG. 19 is a block diagram for showing a configuration of a visual inspection apparatus having a function of a programming apparatus of a visual inspection program in accordance with a third embodiment of the present invention.

A third embodiment of the present invention is described. FIG. 19 shows a block diagram of a visual inspection apparatus 32 having a function of a programming apparatus of the visual inspection program. In comparison with FIG. 19 and FIG. 1, the visual inspection apparatus 32 in the third embodiment comprises an image acquisition unit 7, a visual inspection program memory 15 and a removing unit 16 further to the configuration of the programming apparatus 20 in the first embodiment. The function of the programming apparatus in the third embodiment is substantially the same as one of the programming apparatus in the above-mentioned embodiments, so that the detailed description of the function of the programming apparatus is omitted.

The image acquisition unit 7 is substantially the same as that illustrated in FIG. 2, and used not only for taking the sample image data used in the programming steps of the visual inspection program but also for taking visual images of the products conveyed on the manufacturing line in the actual visual inspection of the products. The inspection program memory 15 is a non-volatile memory such as a hard disc or an EE-PROM (electrically Erasable-Programmable Read Only Memory) for memorizing the visual inspection program programmed by the function of the programming apparatus. The removing unit 16 includes a mechanism such as a removing arm for removing a defective unit of the products from the manufacturing line when the unit is judged as defective by following the visual inspection program. It, however, is possible that the removing unit 16 instructs or marks the defective unit to be removed in a downstream portion in the manufacturing line.

When the programming of the visual inspection program is completed, the inspection processor 6 memorizes the visual inspection program into the visual inspection program memory 15. For executing the visual inspection of the products conveyed in the manufacturing line, the inspection processor 6 reads out the visual inspection program from the visual inspection memory 15 and executes the visual inspection with respect to each image data of the product taken by the image acquisition unit 7 one by one and judges whether the appearance of the product is acceptable or not. When the appearance of the product is judged defective, the inspection processor 6 controls the removing unit 16 for removing the product from the manufacturing line.

By such a configuration, the visual inspection apparatus includes the programming apparatus of the visual inspection program, so that the user of the visual inspection apparatus can easily program the visual inspection program suitable for inspecting the product which the user wishes to inspect.

Industrial Applicability

As mentioned above, the user of the visual inspection apparatus can easily program the visual inspection program suitable for inspecting the products which the user wishes to inspect by following the guidance displayed on the monitor display of the display unit of the programming apparatus of the visual inspection program in accordance with the present invention, even though the user is unaccustomed to the programming language and/or the image processing. Furthermore, the provisional visual inspection program programmed by the programming apparatus is evaluated by actually inspecting the sample image data including the defective units and the non-defective units of the product, so that the reliability and the accuracy of the visual inspection can be increased. Especially, when the result of the evaluation of the provisional visual inspection program is improper, it is possible to compensate the provisional visual inspection program by changing at least one image processing algorithm and/or at least one inspection parameter until the evaluation of the provisional visual inspection program becomes proper. Finally, the provisional visual inspection program evaluated proper is outputted as the visual inspection program, so that the result of the visual inspection of the products conveyed on the manufacturing line by the visual inspection apparatus using the visual inspection program rarely includes erroneous component.

What is claimed is:

1. A programming apparatus of a visual inspection program comprising:

an image data memory that stores a plurality of user prepared sample image data of defective units and non-defective units of an object to be inspected;

an algorithm memory that stores a plurality of image processing algorithms with respect to each inspection object;

a standard flow memory that stores at least one standard inspection flow and a plurality of inspection parameters with respect to each kind of object to be inspected;

a display unit having a monitor display for displaying at least a guidance of programming steps;

an input unit configured for inputting or selecting a kind of an object to inspected, and for selecting at least one image processing algorithm and at least one inspection parameter; and an inspection processor for displaying the guidance of the programming steps, automatically selecting a standard inspection flow from the standard flow memory corresponding to the input or selection of the kind of the object, reading at least one image processing algorithm from the algorithm memory and at least one inspection parameter from the standard flow memory corresponding to the selection, programming a provisional visual inspection program by using the standard inspection flow, at least one image processing algorithm and at least one inspection parameter, processing the sample image data of defective units and non-defective units by following the provisional visual inspection program, executing the visual inspection to determine whether an appearance of the object with respect to each sample image data is defective or non-defective using processed image data, displaying results of the visual inspection of the sample image data on the monitor display of the display unit, requiring a judgment whether the provisional visual inspection program is proper or improper, and outputting the provisional visual inspection program as a final visual inspection program upon a judgment that the provisional visual inspection program is proper.

2. The programming apparatus in accordance with claim 1, wherein the inspection processor further requires the changing at least one image processing algorithm and/or at least one inspection parameter upon a judgment that the provisional visual inspection program is improper.

3. The programming apparatus in accordance with claim 2, wherein the inspection processor repeats the requirement for changing the at least one image processing algorithm and/or at least one inspection parameter until the provisional visual inspection program is judged proper.

4. The programming apparatus in accordance with claim 1, wherein the image data memory stores with each sample image data of the defective units with an information of a cause of a defect.

5. The programming apparatus in accordance with claim 1, wherein the sample image data of the defective units and non-defective units are respectively sorted in the image data memory based upon a degree of defect and a degree of quality.

6. The programming apparatus in accordance with claim 1, wherein the sample image data of the defective units and non-defective units are sorted in the image data memory based upon illumination methods or condition when the sample image data are taken.

7. The programming apparatus in accordance with claim 1, wherein the standard flow memory stores the standard inspection flow with at least one inspection parameter corresponding to a surface nature or a material of the object.

8. The programming apparatus in accordance with claim 1, wherein the standard flow memory stores the standard inspection flow with at least one inspection parameter corresponding to a surface color of the object.

9. The programming apparatus in accordance with claim 1, wherein the standard flow memory stores a combination of a standard inspection flow, at least one image processing algorithm and at least one inspection parameter recommended by an expert with respect to each kind of the object.

10. The programming apparatus in accordance with claim 1, wherein the standard flow memory stores a combination of a standard inspection flow, a plurality of image processing algorithms and at least one inspection parameter, precedence being given to the image processing algorithm recommended by an expert with respect to each kind of the object.

11. The programming apparatus in accordance with claim 1, wherein the standard flow memory stores a combination of a standard inspection flow, at least one image processing algorithm and a plurality of inspection parameters, precedence being given to the inspection parameters recommended by an expert with respect to each kind of the object.

12. The programming apparatus in accordance with claim 1, wherein the standard flow memory stores an initial value of each inspection parameter, a width and directions for changing the value of each inspection parameter, and an upper limit and a lower limit of a region within which the value of each inspection parameter is varied.

13. The programming apparatus in accordance with claim 1, wherein the inspection processor compares the result of the visual inspection with respect to each sample image data with defectiveness or non-defectiveness of the sample inspected in the visual inspection, counts a number of the result of the inspection regarding the defectiveness or non-defectiveness of the sample, and repeats the visual inspection of the sample image data with changing of the inspection parameter until the counted number reaches to a predetermined value.

14. The programming apparatus in accordance with claim 1, the inspection processor repeatedly requiring the changing of an inspection parameter until the counted number reaches a predetermined value.

15. The programming apparatus in accordance with claim 1, wherein the inspection processor further displays at least one image using a sample image data on the monitor display of the display unit.

16. The programming apparatus in accordance with claim 15, wherein a region to be inspected on a surface of the object is selected by defining at least two points by using the input unit while the image of the object is displayed on the monitor display of the display unit.

17. The programming apparatus in accordance with claim 15, wherein the inspection processor displays images before and after the image processing of each sample image data on the monitor display of the display unit.

18. The programming apparatus in accordance with claim 1, wherein the inspection processor further displays a table that shows the visual inspection results with respect to all the sample image data, on the monitor display of the display unit.

19. The programming apparatus in accordance with claim 18, wherein the inspection processor displays images before and after the image processing of a sample image data in the table on the monitor display of the display unit when the user selects a point on the monitor display corresponding to the sample data.

20. The programming apparatus in accordance with claim 1, further comprising a data communication unit for outputting the visual inspection program to an external visual inspection apparatus.

21. The programming apparatus in accordance with claim 1, further comprising a recording apparatus for recording the visual inspection program in a recording medium.

22. The programming apparatus in accordance with claim 1, further comprising an image acquisition apparatus that receives the sample image data.

23. A visual inspection apparatus comprising an image acquisition unit for taking an image data of an object conveyed on a manufacturing line; a visual inspection unit for performing predetermined image processing to the image data taken by the image acquisition unit and for judging whether an appearance of the object is defective or non-defective by following a visual inspection program; a remover for removing the object or for instructing removal of the object judged defective from the manufacturing line; and a visual inspection programmer for programming a visual inspection program suitable for inspecting the object, the visual inspection programming unit further comprising:

an image data memory that stores a plurality of user prepared sample image data of defective units and non-defective units of the object to be inspected;

an algorithm memory that stores a plurality of image processing algorithms with respect to each inspection object;

a standard flow memory that stores at least one standard inspection flow and a plurality of inspection parameters with respect to each kind of the object to be inspected;

a display unit having a monitor display for displaying at least a guidance of programming steps;

an input unit configured for inputting or selecting a kind of an object to be inspected, and for selecting at least one image processing algorithm and at least one inspection parameter; and an inspection processor for displaying the guidance of the programming steps, automatically selecting a standard inspection flow from the standard flow memory corresponding to the input or selection of the kind of the object, reading at least one image processing algorithm from the algorithm memory and at least one inspection parameter from the standard flow memory corresponding to the input or selection, programming a provisional visual inspection program by using the standard inspection flow, at least one image processing algorithm and at least one inspection parameter, processing the sample image data of defective units and non-defective units by following the provisional visual inspection program, executing the visual inspection to determine whether an appearance of the object with respect to each sample image data is defective or non-defective using processed image data, displaying results of the visual inspection of the sample image data on the monitor display of the display unit, requiring a judgment whether the provisional visual inspection program is proper or improper, and outputting the provisional visual inspection program as a final visual inspection program upon a judgment that the provisional visual inspection program is proper.

24. A method for performing a visual inspection program comprising:

storing a plurality of image processing algorithm with respect to each inspection object, at least one standard inspection flow and a plurality of inspection parameters with respect to each kind of object to be inspected;

requiring input or selection of a kind of the object to be inspected;

requiring input of a plurality of sample image data of defective units and non-defective units of the object to be inspected;

automatically selecting a standard inspection flow corresponding to the kind of the object among the previously stored standard inspection flows;

requiring selection of at least one image processing algorithm and at least one inspection parameter of the stored image processing algorithms and the inspection parameters by following the selected standard inspection flow;

programming a provisional visual inspection program using the selected standard inspection flow, the image processing algorithm and the inspection parameter;

reading out the sample image data sequentially;

executing visual inspection of the sample image data by following the provisional visual inspection program;

executing the visual inspection with respect to each sample image data to judge whether an appearance of the object is defective or non-defective; and displaying the result of the judgment of the visual inspection of the sample image data on a monitor display.

25. A program stored on a computer readable medium for programming a visual inspection program, the program comprising the:

requiring user input or selection of a kind of an object to be inspected;

automatically selecting a standard inspection flow from a previously input plurality of standard inspection flows corresponding to the input or selection of the kind of the object;

requiring input of a plurality of sample image data of the object including at least one defective unit and at least one non-defective unit;

requiring selection of at least one image processing algorithm and at least one inspection parameter of a plurality of image processing algorithms and a plurality of inspection parameters;

programming a provisional visual inspection program using the selected standard inspection flow, the image processing algorithm and the inspection parameter;

reading the sample image data sequentially;

executing the visual inspection with each sample image data in accordance with the provisional visual inspection program;

judging whether the sample image data is defective or non-defective; and displaying the result of the judgment with respect to all the sample image data on a monitor display.

26. A computer readable recording medium storing at least one standard inspection flow with respect to each kind of object to be inspected, a plurality of image processing algorithms with respect to each inspection object, a plurality of inspection parameters and a program for programming a visual inspection program, wherein the program comprises:

requiring user input or a selection of a kind of object to be inspected;

requiring input of a plurality of previously prepared sample image data of defective units and non-defective units of objects to be inspected;

automatically selecting a standard inspection flow corresponding to the kind of the object from the stored standard inspection flows;

requiring selection of at least one image processing algorithm and at least one inspection parameter from the stored image processing algorithms and the inspection parameters in accordance with the selected standard inspection flow;

programming a provisional visual inspection program using the selected standard inspection flow, the image processing algorithm and the inspection parameter;

sequentially reading out the sample image data for executing visual inspection by following a provisional visual inspection program configured by the selected standard inspection flow, image processing algorithm and inspection parameter;

executing the visual inspection with respect to each sample image data and judging whether an appearance of the object is defective or non-defective in accordance with the provisional visual inspection program; and displaying the result of the judgment of the visual inspection of the sample image data on a monitor display.

* * * * *

UNITED STATES PATENT AND TRADEMARK OFFICE
CERTIFICATE OF CORRECTION

PATENT NO. : 6,922,481 B2
DATED : July 26, 2005
INVENTOR(S) : T. Masuda et al.

It is certified that error appears in the above-identified patent and that said Letters Patent is hereby corrected as shown below:

Column 21,
Line 17, after "to" insert -- be --.

Column 24,
Line 60, after "or" delete "a".

Signed and Sealed this

Sixth Day of June, 2006

JON W. DUDAS
*Director of the United States Patent and Trademark Office*